(12) United States Patent
Schlienger

(10) Patent No.: US 7,727,999 B2
(45) Date of Patent: *Jun. 1, 2010

(54) SPIROAZACYCLIC COMPOUNDS AS MONOAMINE RECEPTOR MODULATORS

(75) Inventor: Nathalie Schlienger, Frederiksberg (DK)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/360,478

(22) Filed: Jan. 27, 2009

(65) Prior Publication Data

US 2009/0131418 A1 May 21, 2009

Related U.S. Application Data

(60) Continuation of application No. 11/687,552, filed on Mar. 16, 2007, now Pat. No. 7,511,053, which is a continuation of application No. 11/154,083, filed on Jun. 16, 2005, now Pat. No. 7,217,719, which is a division of application No. 10/329,719, filed on Dec. 23, 2002, now Pat. No. 6,911,452.

(60) Provisional application No. 60/344,750, filed on Dec. 28, 2001.

(51) Int. Cl.
C07D 498/10 (2006.01)
A61K 31/438 (2006.01)
A61P 25/24 (2006.01)

(52) U.S. Cl. .............................. 514/278; 546/17; 546/18
(58) Field of Classification Search .................... 546/17, 546/18; 514/278
See application file for complete search history.

(56) References Cited

U.S. PATENT DOCUMENTS

| | | | |
|---|---|---|---|
| 3,983,234 A | 9/1976 | Sayers | |
| 4,138,492 A | 2/1979 | Noverola et al. | |
| 4,255,432 A | 3/1981 | Kluge et al. | |
| 4,332,804 A | 6/1982 | Clark | |
| 4,353,900 A | 10/1982 | Clark | |
| 4,353,901 A | 10/1982 | Clark | |
| 4,367,232 A | 1/1983 | Boix-Igleasias et al. | |
| 4,853,394 A | 8/1989 | King et al. | |
| 5,025,013 A | 6/1991 | Barreau et al. | |
| 5,214,055 A | 5/1993 | Peglion et al. | |
| 5,216,165 A | 6/1993 | Mobilio et al. | |
| 5,461,066 A | 10/1995 | Gericke et al. | |
| 5,595,872 A | 1/1997 | Wetterau, II et al. | |
| 5,621,010 A | 4/1997 | Sueda et al. | |
| 5,707,798 A | 1/1998 | Brann | |
| 5,795,894 A | 8/1998 | Shue et al. | |
| 5,869,488 A | 2/1999 | Shue et al. | |
| 5,877,173 A | 3/1999 | Olney et al. | |
| 5,912,132 A | 6/1999 | Brann | |
| 5,955,281 A | 9/1999 | Brann | |
| 6,107,324 A | 8/2000 | Behan et al. | |
| 6,140,509 A | 10/2000 | Behan et al. | |
| 6,150,393 A | 11/2000 | Behan et al. | |
| 6,248,756 B1 | 6/2001 | Anthony et al. | |
| 6,358,698 B1 | 3/2002 | Weiner et al. | |
| 6,399,619 B1 | 6/2002 | Berk et al. | |
| 6,756,393 B2 | 6/2004 | Andersson et al. | |
| 6,815,458 B2 | 11/2004 | Andersson et al. | |
| 6,911,452 B2 | 6/2005 | Schlienger | |
| 7,022,698 B2 | 4/2006 | Hamied et al. | |
| 7,041,667 B1 | 5/2006 | Armour et al. | |
| 7,115,634 B2 | 10/2006 | Thurieau et al. | |
| 7,217,719 B2 | 5/2007 | Schlienger | |
| 7,253,186 B2 | 8/2007 | Andersson et al. | |
| 7,351,707 B2 | 4/2008 | Schlienger | |
| 7,402,590 B2 | 7/2008 | Schlienger | |
| 7,476,682 B2 | 1/2009 | Andersson et al. | |
| 7,511,053 B2 | 3/2009 | Schlienger | |
| 2004/0006081 A1 | 1/2004 | Burrows et al. | |
| 2004/0106600 A1 | 6/2004 | Andersson et al. | |
| 2004/0213816 A1 | 10/2004 | Weiner et al. | |
| 2005/0014757 A1 | 1/2005 | Andersson et al. | |
| 2005/0148018 A1 | 7/2005 | Weiner et al. | |
| 2005/0244862 A1 | 11/2005 | Brann | |
| 2005/0256108 A1 | 11/2005 | Schlienger | |
| 2006/0094758 A1 | 5/2006 | Andersson et al. | |
| 2006/0106063 A1 | 5/2006 | Thygesen et al. | |
| 2006/0111399 A1 | 5/2006 | Thygesen et al. | |

(Continued)

FOREIGN PATENT DOCUMENTS

CA 984843 3/1976

(Continued)

OTHER PUBLICATIONS

Adam, et al. 1989. Effects of repeated ritanserin on middle-aged poor sleepers. *Psychopharmacology*, 99:219-221.

(Continued)

Primary Examiner—Kahsay T Habte
(74) Attorney, Agent, or Firm—Knobbe Martens Olson & Bear LLP

(57) ABSTRACT

The present invention relates to optionally substituted 1,3,8-triaza-spiro[4.5]decan-2-one compounds as monoamine receptor modulators; compositions comprising the same; methods of inhibiting an activity of a monoamine receptor with said compounds; methods of treating a disease condition associated with a monoamine receptor using said compounds; and methods for identifying a subject suitable for treatment using said compounds.

16 Claims, 2 Drawing Sheets

U.S. PATENT DOCUMENTS

| | | |
|---|---|---|
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |
| 2006/0205710 A1 | 9/2006 | Schlienger |
| 2006/0205722 A1 | 9/2006 | Andersson et al. |
| 2006/0205780 A1 | 9/2006 | Thygesen et al. |
| 2006/0205781 A1 | 9/2006 | Thygesen et al. |
| 2006/0264465 A1 | 11/2006 | Weiner et al. |
| 2006/0264466 A1 | 11/2006 | Weiner et al. |
| 2006/0286610 A1 | 12/2006 | Brann |
| 2006/0292606 A1 | 12/2006 | Brann |
| 2007/0161621 A1 | 7/2007 | Schienger |
| 2009/0131418 A1 | 5/2009 | Schienger |
| 2009/0186921 A1 | 7/2009 | Andersson et al. |

FOREIGN PATENT DOCUMENTS

| | | |
|---|---|---|
| EP | 0 005 318 A1 | 11/1979 |
| EP | 0 061 333 A1 | 9/1982 |
| EP | 0 379 441 A1 | 7/1990 |
| EP | 0 548 015 A1 | 6/1993 |
| EP | 0 260 070 B1 | 8/1993 |
| EP | 0 625 507 A2 | 11/1994 |
| FR | 2802206 A1 | 6/2001 |
| HU | 157325 | 3/1998 |
| JP | 09-503491 | 4/1997 |
| WO | WO 94/27967 A1 | 12/1994 |
| WO | WO 95/03303 | 2/1995 |
| WO | WO 97/08166 A1 | 3/1997 |
| WO | WO 97/11940 A1 | 4/1997 |
| WO | WO 97/38665 A2 | 10/1997 |
| WO | WO 97/38984 A1 | 10/1997 |
| WO | WO 98/11128 A1 | 3/1998 |
| WO | WO 98/17646 A1 | 4/1998 |
| WO | WO 98/44921 A1 | 10/1998 |
| WO | WO 98/50534 A1 | 11/1998 |
| WO | WO 99/52927 A1 | 10/1999 |
| WO | WO 00/23076 A1 | 4/2000 |
| WO | WO 00/56335 A1 | 9/2000 |
| WO | WO 00/59497 A1 | 10/2000 |
| WO | WO 00/69810 A1 | 11/2000 |
| WO | WO 01/44191 A1 | 6/2001 |
| WO | WO 01/66521 A1 | 9/2001 |
| WO | WO 01/87839 A1 | 11/2001 |
| WO | WO 02/079186 A2 | 10/2002 |
| WO | WO 03/057698 A2 | 7/2003 |
| WO | WO 03/057698 A3 | 7/2003 |
| WO | WO 03/062206 A2 | 7/2003 |
| WO | WO 03/062206 A3 | 7/2003 |
| WO | WO 03/070246 A1 | 8/2003 |
| WO | WO 03/086400 A1 | 10/2003 |
| WO | WO 04/000808 A2 | 12/2003 |
| WO | WO 04/000808 A3 | 12/2003 |
| WO | WO 2004/009549 A2 | 1/2004 |
| WO | WO 2004/039322 A2 | 5/2004 |
| WO | WO 2004/064738 A2 | 8/2004 |
| WO | WO 2004/064738 A3 | 8/2004 |
| WO | WO 2004/064753 A2 | 8/2004 |
| WO | WO 2004/072034 A1 | 8/2004 |
| WO | WO 2005/063254 A2 | 7/2005 |
| WO | WO 2005/112927 A | 12/2005 |
| WO | WO 2006/036874 A1 | 4/2006 |
| WO | WO 2006/037043 A1 | 4/2006 |

OTHER PUBLICATIONS

Adell, et al. 2005. Strategies for producing faster acting antidepressants. *Drug Discovery Today*, 10(8):578-585.

Akin, et al. 2004. Decreased serotonin 5-$HT_{2A}$ receptor-stimulated phosphoinositide signaling in fibroblasts from melancholic depressed patients. *Neuropsychopharmacology*, 29:2081-2087.

Alvisi, N. 1892. Sulla formazione di derivati pirazolici dalle dicloridrine e dalla tribromidrina della glicerina ordinaria, *Gazz. Chem. Ital.* 22:158-168.

Antilla, et al. 2001. Copper-catalyzed coupling of arylboronic acids and amines. *Organic Letters*, 3(13):2077-2079.

Antilla, et al. 2002. The copper-catalyzed N-arylation of indoles. *J. Am. Chem. Soc.*, 124:11684-11688.

Archibald, et al., 1974 "Benzamidopiperdines. 2. Heterocyclic Compounds Related to Indoramin" *J. Medicinal Chemistry*, 17(7):736-739.

Archibald, et al., 1974 "Benzamidopiperdines. 3. Heterocyclic Compounds Related to Indoramin" J. Medicinal Chemistry, 17(7):-739-744.

Archibald, et al., 1974 "1,4-Bis-(2-indol-3-ylethyl)piperdines" J. Medicinal Chemistry, 17(7):-745-747.

Artico, et al. 1992. Aromatic hydrazides as specific inhibitors of bovine serum amine oxidase. *Eur. J. Med. Chem.*, 27:219-228.

Bakshi, et al. 1994. Clozapine antagonizes phencyclidine-induced deficits in sensorimotor gating of the startle response. *The Journal of Pharmacology and Experimental Therapeutics*, 271(2):787-794.

Barchas, J. 1973. *Serotonin and Behavior*. New York: Academic Press.

Barnes, et al. 1999. A review of central 5-HT receptors and their function. *Neuropharmacology*, 38:1083-1152.

Barr, et al. 1997. Agonist-independent activation of $G_z$ by the 5-hydroxytryptamine$_{1A}$ receptor co-expressed in *Spodoptera frugiperda* cells. *The Journal of Biological Chemistry*, 272(52):32979-32987.

Bassus, et al. 1974. Psychotropes potentiels. X. Synthèse de butyrophénones à cycle pipéridine-spiro-tétrahydrooxazinone douées d'activité neuroleptique. *Eur. J. Med. Chem.—Chimica Therapeutica*, 9(4):416-423.

Bennett, et al. 1993. Suppression of dyskinesias in advanced Parkinson's disease. II. Increasing daily clozapine doses suppress dyskinesias and improve parkinsonism symptoms. *Neurology*, 43:1551-1555.

Bhatia, et al. 1996. 5-Lipoxygenase inhibitors: Synthesis and structure-activity relationships of a series of 1-Aryl-2H,4H-tetrahydro-1,2,4-triazin-3-ones. *J. Med. Chem.*, 39:3938-3950.

Biagi, et al. 1988. 1,2,3-Triazoles: Structural changes on two effective inhibitors of the prostaglandin synthesis in vitro. *Farmaco Ed. Sci.*, 43:597-612.

Bibbiani, et al. 2001. Serotonin 5-HT1A agonist improves motor complications in rodent and primate parkinsonian models. *Neurology*, 57:1829-1834.

Birkmayer, et al. 1974. Nucleus ruber and L-Dopa psychosis: Biochemical post-mortem findings. *Journal of Neural Transmission*, 35:93-116.

Blakley, et al. 2001. Bidirectional changes in ethanol consumption in rats with site-specific antisense down-regulation of 5-hydroxytryptamine$_{2A}$ receptors in brain. *The Journal of Pharmacology and Experimental Therapeutics*, 299(1):277-289.

Blier, et al. 2001. Putative mechanisms of action of antidepressant drugs in affective and anxiety disorders and pain. *Journal of Psychiatry & Neuroscience*, 26(1):37-43.

Blier, et al. 2005. Potential mechanisms of action of atypical antipsychotic medications in treatment-resistant depression and anxiety. *J. Clin. Psychiatry*, 66(suppl 8):30-40.

Bond et al. 1995. Physiological effects of inverse agonists in transgenic mice with myocardial overexpression of the $\beta_2$-adrenoceptor. *Nature*, 374:272-276.

Boullin D. J. 1978. *Serotonin in Mental Abnormalities* (p. 316). New York: Wiley.

Brown, et al. 1924. Catalytic alkylation of aniline, *J. Am. Chem. Soc.*, 46(8):1836-1839.

Buchi et al. 1969. Synthesis of (±)-nuciferal. *J. Org. Chem.*, 34(4):1122-1123.

Butcher, et al. 1970. L-Dopa induced changes in central monoamine neurons after peripheral decarboxylase inhibition. *Letters to the Editor, J. Pharm. Pharmac.*, 22:313-316.

Buu-Hoi, et al. 1951. Further studies in the alkylation of phenols and thiophenols, *J. Org. Chem.*, 16:988-994.

Cacchi, et al. 2003. Palladium-catalyzed reaction of aryl iodides with acetic anhydride. A carbon monoxide-free synthesis of acetophenones. *Organic Letters*, 5(3):289-291.

Carman, et al. 1998. A further synthesis of an analogue of the antifungal/antiherbivore lipid from avocado. *Aust. J. Chem.*, 51:955-959.

Carroll, et al. 1992. Synthesis and muscarinic receptor activity of ester derivatives of 2-substituted 2-azabicyclo[2.2.1]heptan-5-ol and -6-ol. *J. Med. Chem.*, 35:2184-2191.

Catarzi, et al. 2001. Synthesis, ionotropic glutamate receptor binding affinity, and structure-activity relationships of a new set of 4,5-dihydro-8-heteroaryl-4-oxo-1,2,4-triazolo[1,5-*a*]quinoxaline-2-carboxylates analogues of TQX-173. *J. Med Chem.*, 44:3157-3165.

Cerione, et al. 1984. The mammalian $\beta_2$-adrenergic receptor: Reconsitution of functional interactions between pure receptor and pure stimlatory nucelotide binding protein of the adenylate cyclase system. *Biochemistry*, 23:4519-4525.

Chemical Abstracts, 128:111548. Brann, M. R. 1998. Identification of ligands by selective amplification of cells transfected with receptors and marker enzymes.

Cherkasov, et al. 1985. Organothiophosphorus reagents in organic synthesis. *Tetrahedron*, 41(13):2567-2624.

Clark et al. 1983. Antihypertensive 9-substituted 1-Oxa-4,9-diazaspiro[5.5]undecan-3-ones. *J. Med. Chem.*, 26:855-861.

DeClerck, et al. 1987. Increase in slow-wave sleep in humans with the serotonin-$S_2$ antagonist ritanserin. *Current Therapeutic Research*, 41(4):427-432.

Dunn, et al. 1986. Analgetic and antiinflammatory 7-aroylbenzofuran-5-ylacetic acids and 7-aroylbenzothiophene-5-ylacetic acids. *J. Med. Chem.*, 29:2326-2329.

Durif, et al. 1997. Low-dose clozapine improves dyskinesias in Parkinson's disease. *Neurology*, 48:658-662.

Eichelbaum, et al. 1996. Influence of pharmacogenetics on drug disposition and response. *Clinical and Experimental Pharmacology and Physiology*, 23:983-985.

Emerson, et al. 1938. The reductive alkylation of aniline. *J. Am. Chem. Soc.*, 60:2023-2025.

Ermakov, et al. 1981. Use of Mass spectrometry in structural and stereochemical studies. *Chemistry of Heterocyclic Compounds*, 1:72-77.

Everett, et al. 1970. L-Dopa: Effect on concentrations of dopamine, norepinephrine, and serotonin in brains of mice. *Science*, 168:849-850.

Finar, et al. 1954. The preparation and properties of some derivatives of 1-phenylpyrazole, *J. Chem. Soc.*, pp. 2293-2298.

Fišera, et al. 1994. Synthesis of spiro-substituted 1,3-oxazines by a new sequence leading to spiroheterocycles. *Monatshefte für Chemie*, 125:909-919.

Friedman, et al. 1999. Low-dose clozapine for the treatment of drug-induced psychosis in Parkinson's disease. *N. Engl. J. Med.*, 340(10):757-763.

Friedman, et al. 2000. Atypical antipsychotics in the treatment of drug-induced psychosis in Parkinson's disease. *Movement Disorders*, 15(2):201-211.

Fuller, R. W. 1982. Drugs acting on serotonergic neuronal systems. In N. N. Osborne (Ed.), *Biology of Serotonergic Transmission*, Chap. 9, pp. 221-247. New York: Wiley.

Gainetdinov, et al. 2001. Genetic animal models: Focus on schizophrenia. *Trends in Neurosciences*, 24(9)527-533.

Gamma, et al. 2000. 3,4-Methylenedioxymethamphetamine (MDMA) modulates cortical and limbic brain activity as measured by $[H_2{}^{15}O]$-PET in healthy humans. *Neuropsychopharmacology*, 23(4):388-395.

Gawley, R. E., & Aubé, J. 1996. *Principles of Asymmetric Synthesis*. New York: Pergamon.

Gershon, M. D., Mawe, G. M., & Branchek, T. A. 1989. 5-Hydroxytryptamine and enteric neurones. In J. R. Fozard (Ed.), *The Peripheral Actions of 5-Hydroxytryptamine* (pp. 247-273). New York: Oxford University Press.

Gillman, P. K. 2005. Monoamine oxidase inhibitors, opioid analgesics and serotonin toxicity. *British Journal of Anaesthesia*, 95(4):434-441.

Glennon, R. A. 1990. Serotonin receptors: Clinical implications. *Neuroscience & Biobehavioral Reviews*, 14:35-47.

Gooβen, et al. 2001. Palladium-catalyzed synthesis of aryl ketones from boronic acids and carboxylic acids or anhydrides. *Angew. Chem. Int. Ed.*, 40:3458-3460.

Gstach et al. 1990. Rearrangement of 3,3-disubstituted 1-aryl-4,5-dihydro-5-oxo-3*H*-1,2,4-triazolium tetrafluoroborates; Part 1. A versatile synthesis of 1,5-disubstituted 2-aryl-1,2-dihydro-3*H*-1,2,4-triazol-3-one tetrafluoroborates. *Synthesis*, pp. 803-808.

Guthrie, et al. 1993. The tetrahedral intermediate from the hydration of *N*-methylformanilide. *Can. J. Chem.*, 71:2109-2122.

Hartwig, J. F. 1998. Transition metal catalyzed synthesis of arylamines and aryl ethers from aryl halides and triflates: Scope and mechanism. *Angew. Chem. Int. Ed.*, 37:2047-2067.

Hickinbottom, W. J. 1930. The preparation of secondary alkylarylamines and their purification. *J. Chem. Soc.*, pp. 992-994.

Hirst, et al. 1895. A method for preparing the formyl derivatives of the aromatic amines. *J. Chem. Soc.*, 67:829-831.

Idzikowski, et al. 1991. A dose response study examining the effects of ritanserin on human slow wave sleep. *Br. J. Clin. Pharmac.*, 31:193-196.

Irikura et al., 1971 "New Anticulcer Agents. 1. Synthesis and Biological Activities of 1-Acyl-2-,-3-, -4-substituted Benzamidopiperdines" *J. Medicinal Chemistry* 14(4): 357-361.

Jaeger, et al. 1941. Two ketones of the stilboestrol group. *J. Chem. Soc.*, 744-747.

Julius, et al. 1990. The 5HT2 receptor defines a family of structurally distinct but functionally conserved serotonin receptors. *Proc. Natl. Acad. Sci. USA*, 87:928-932.

Kanayama, et al. 2005. New treatment of lumbar disc herniation involving 5-hydroxytryptamine$_{2A}$ receptor inhibitor: A randomized controlled trial. *J. Neurosurg.: Spine*, 2:441-446.

Klapars, et al. 2001. A general and efficient copper catalyst for the amidation of aryl halides and the *N*-arylation of nitrogen heterocycles. *J. Am. Chem. Soc.*, 123:7727-7729.

Klapars, et al. 2002. A general and efficient copper catalyst for the amidation of aryl halides. *J. Am. Chem. Soc.*, 124:7421-7428.

Kuehne, et al. 1991(a). Enantioselective syntheses of vinblastine, leurosidine, vincovaline, and 20'-*epi*-vincovaline. *J. Org. Chem.*, 56(2):513-528.

Kuehne, et al. 1991(b). Total syntheses of *Yohimbe* alkaloids, with stereoselection for the normal, allo, and 3-epiallo series, based on annelations of 4-methoxy-1,2-dihydropyridones. *J. Org. Chem.*, 56(8):2701-2712.

Kwong, et al. 2002(a). Copper-catalyzed coupling of alkylamines and aryl iodides: An efficient system even in an air atmosphere. *Organic Letters*, 4(4):581-584.

Kwong, et al. 2002(b). A general, efficient, and inexpensive catalyst system for the coupling of aryl iodides and thiols. *Organic Letters*, 4(20):3517-3520.

Kwong, et al. 2003. Mild and efficient copper-catalyzed amination of aryl bromides and primary alkylamines. *Organic Letters*, 5(6):793-796.

Landini, et al. 1974. A convenient synthesis of primary and secondary dialkyl and aryl alkyl sulfides in the presence of phase-transfer catalysts. *Synthesis*, pp. 565-566.

Landolt, et al. 1999. Serotonin-2 receptors and human sleep: Effect of a selective antagonist on EEG power spectra. *Neuropsychopharmacology*, 21(3):455-466.

Leysen, et al. 1978. Serotonergic component of neuroleptic receptors. *Nature*, 272:168-171.

Li, G. Y. 2002. Highly active, air-stable palladium catalysts for the C-C and C-S bond-forming reactions of vinyl and aryl cholrides: Use of commercially available $[(t\text{-Bu})_2P(OH)]_2PdCl_2$, $[(t\text{-Bu})_2P(OH)PdCl_2]_2$, and $[[(t\text{-Bu})_2PO \ldots H \ldots OP(t\text{-Bu})_2]PdCl]_2$ as catalysts. *J. Org. Chem.*, 67:3643-3650.

Liechti, et al. 2001. Effects of MDMA (ecstasy) on prepulse inhibition and habituation of startle in humans after pretreament with Citalopram, Haloperidol, or Ketanserin. *Neuropsychopharmacology*, 24(3):240-252.

Linder, et al. 1997. Pharmacogenetics: A laboratory tool for optimizing therapeutic efficiency. *Clinical Chemistry*, 43(2):254-266.

Lowe, et al. 1994. Aza-tricyclic substance P antagonists. *J. Med. Chem.*, 37:2831-2840.

Mansbach, et al. 1988. Dopaminergic stimulation disrupts sensorimotor gating in the rat. *Psychopharmacology*, 94:507-514.

Marek, et al. 2003. Synergistic action of 5-$HT_{2A}$ antagonists and selective serotonin reuptake inhibitors in neuropsychiatric disorders. *Neuropsychopharmacology*, 28:402-412.

Marek, et al. 2005. The selective 5-$HT_{2A}$ receptor antagonist M100907 enhances antidepressant-like behavioral effects of the SSRI fluoxetine. *Neuropsychopharmacology*, 30:2205-2215.

Mavunkel, et al. 1996. Synthesis and characterization of pseudopeptide bradykinin B2 receptor antagonists containing the 1,3,8-triazaspiro[4.5]decan-4-one ring system. *J. Med. Chem.*, 39:3169-3173.

Mayer, et al. 2003. Ritanserin improves sleep quality in narcolepsy. *Pharmacopsychiatry*, 364:150-155.

Meltzer, et al. 1995. Plasma clozapine levels and the treatment of L-DOPA-induced psychosis in Parkinson's disease. *Neuropsychopharmacology*, 12(1):39-45.

Meltzer, H. Y. 1999. The role of serotonin in antipsychotic drug action. *Neuropsychopharmacology*, 21(2S):106S-115S.

Meng, et al. 1991. Synthetic approaches toward glidobamine, the core structure of the glidobactin antibiotics. *Tetrahedron*, 47(32):62510-6264.

Micovic, et al. 1991. A simple method for preparation of secondary aromatic amines. *Synthesis*, 11:1043-1045.

Miyata, et al. 2000. Sarpogrelate, a selective 5-$HT_{2A}$ serotonergic receptor antagonist, inhibits serotonin-induced coronary artery spasm in a porcine model. *Journal of Cardiovascular Pharmacology*, 35(2) 294-301.

Moulignier, A. 1994. Récepteurs centraux de la sérotonine principaux aspects fondamentaux et fonctionnels application thérapeutiques. *Rev. Neurol.*, 150:3-15.

Moulignier, A. 1994. Récepteurs centraux de la sérotonine principaux aspects fondamentaux et fonctionnels application thérapeutiques. *Rev. Neurol.*, 150:3-15.

Moune, et al. 1997. Total synthesis of dolatrienoic acid: A subunit of dolastatin 14. *J. Org. Chem.*, 62:3332-3339.

Mullen et al. 2000. (−)-Spiro[1-azabicyclo[2.2.2]octane-3,5'-oxazolidin-2'one], a conformationally restricted analogue of acetylcholine, is a highly selective full agonist at the α7 nicotinic acetylcholine receptor. *J. Med. Chem.*, 43:4045-4050.

Muri, et al. 1998. Synthesis of new benzylic ethers of oximes derived from 1-phenyl-pyrazole compounds. *Synthetic Communications*, 28(7):1299-1321.

Ng, et al. 1970. L-dopa-induced release of cerebral monoamines. *Science*, 170:76-77.

Nigam, et al. 1957a. Studies with acetylenes. Part II. Some reactions of Grignard reagents with propargylic halides. Model linoleic and linolenic acid systems. *J. Chem Soc.*, pp. 3868-3873.

Nigam, et al. 1957b. The conversion of fatty acids into aldehydes. *J. Chem. Soc.*, pp. 3320-3321.

Nordstrom, et al. 1993. High 5-$HT_2$ receptor occupancy in clozapine treated patients demonstrated by PET. *Psychopharmacology*, 110:365-367.

Ogawa, et al. 2005. Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis. European Journal of Pharmacology, 521:156-163.

Olah, et al. 1956. Notiz über die *n*-formylierung von aminen mit formylfluorid. *Chem. Ber.*, 89:2211-2212.

Old, et al. 2002. Efficient palladium-catalyzed *n*-arylation of indoles. *Organic Letters*, 2(10):1403-1406.

Pace, et al. 1991. A mutant α subunit of $G_{i2}$ induces neoplastic transformation of Rat-1 cells. *Proc. Natl. Acad. Sci. USA*, vol. 88:7031-7035.

Paiva, et al. 1988. Effects of ritanserin on sleep disturbances of dysthymic patients. *Psychopharmacology*, 96:395-399.

Patel, et al. 2004. The highly selective 5-hydroxytryptamine (5-HT)$_{2A}$ receptor antagonist, EMD 281014, significantly increases swimming and decreases immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals. *The Journal of Pharmacology and Experimental Therapeutics*, 275(1):502-508.

Pollak, et al. 1999. Clozapine in drug-induced psychosis in Parkinson's disease. *The Lancet*, 353:2041-2042.

Read, W. T. 1922. Researches on hydantoins. Synthesis of the soporific, 4,4-phenylethyl-hydantoin(nirvanol). *J. Am. Chem. Soc.*, 44:1746-1755.

Ricci, A. 2000. *Modern Amination Methods*. New York: Wiley-VCH.

Rice, et al. 1955. Raney nickel catalyzed n-alkylation of aniline and benzidine with alcohols. *J. Am. Chem. Soc.*, 77:4052-4054.

Rubiralta, M., Giralt, E., & Diez, A. 1991. *Studies in Organic Chemistry 43. Piperidine: Structure, Preparation, Reactivity and Synthetic Applications of Piperidine and its Derivatives*. New York: Elsevier.

Sadzot, et al. 1989. Hallucinogenic drug interactions at human brain 5-$HT_2$ receptors: Implications for treating LSD-induced hallucinogenesis. *Psychopharmacology*, 98:495-499.

Saltzman, et al. 1991. Cloning of the human serotonin 5-HT2 and 5-HT1C receptor subtypes. *Biochemical and Biophysical Research Communications*, 181(3):1469-1478.

Saxena, et al. 1990. Cardiovascular effects of serotonin agonists and antagonists. *Journal of Cardiovascular Pharmacology*, 15(Supp. 7):S17-S34.

Scheibye, et al. 1978. Studies on organophosphorus compounds XXI. The dimer of *p*-methoxyphenylthionophosphine sulfide as thiation reagent. A new route to thiocarboxamides. *Bull. Soc. Chim. Belg.*, 87:229-238.

Schins, et al. 2003. Increased coronary events in depressed cardiovascular patients: 5-$HT_{2A}$ receptor as missing link? *Psychosomatic Medicine*, 65:729-737.

Screttas, et al. 1978. Hydrolithiation of β-olefins by a regiospecific two-step process. Transformation of alkyl phenyl sulfides to alkyl-lithium reagents. *J. Org. Chem.*, 43(6):1064-1071.

Sharpley, et al. 1994. Slow wave sleep in humans: Role of 5-$HT_{2A}$ and 5-$HT_{2C}$ receptors. *Neuropharmacology*, 33(3/4):467-471.

Stefancich, et al. 1984. Agenti antiinfiammatori non-steroidei: Nota III—sintesi ed attività analgesica-antiinfiammatoria di 4-(pirrol-1-il)-fenilacetamidi e di 4-(pirrol-1-il)fenetilamine. *Farmaco Ed. Sci.*, 39(9):752-764.

Stryjer, et al. 2003. Treatment of neuroleptic-induced akathisia with the 5-$HT_{2A}$ antagonist trazodone. *Clinical Neuropharmacology*, 26(3):137-141.

Tolstikov et al.1991 "Synthesis and Reactivity of N-substituted aminoamides, antiarrhythmic and local anaesthetic activity" *Russian Chemical Reviews* 60(4):420434.

Tsukamoto, et al. 1995. Synthesis and structure-activity studies of a series of 1-oxa-2,8-diazaspiro[4.5]decan-3-ones and related compounds as $M_1$ muscarinic agonists. *Chem. Pharm. Bull.*, 43(9):1523-1529.

Vallar, et al. 1987. Altered $G_s$ and adenylate cyclase activity in human GH-secreting pituitary adenomas. *Nature*, 330:566-568.

Van Laar, et al. 2001. Subchronic effects of the GABA-agonist lorazepam and the 5-$HT_{2A/2C}$ antagonist ritanserin on driving performance, slow wave sleep and daytime sleepiness in healthy volunteers. *Psychopharmacology*, 154:189-197.

Varma, et al. 1999. Microwave-accelerated solvent-free synthesis of thioketones, thiolactones, thioamides, thionoesters, and thioflavonoids. *Organic Letters*, 1(5):697-700.

Viola, et al. 2002. Ritanserin, a serotonin-2 receptor antagonist, improves ultradian sleep rhythmicity in young poor sleepers. *Clinical Neurophysiology*, 113:429-434.

Vogel, A. I. 1948. Physical properties and chemical constitution. Part XIX. Five-membered and six-membered carbon rings. *J. Chem. Soc.*, pp. 1809-1813.

Vogl, et al. 2002. Palladium-catalyzed monoarylation of nitroalkanes. *J. Org. Chem.*, 67(1):106-111.

Weiner, et al. 2001. 5-Hydroxytryptamine$_{2A}$ receptor inverse agonists as antipsychotics. *The Journal of Pharmacology and Experimental Therapeutics*, 299(1):268-276.

Whitmore, et al. 1942. Abnormal Grignard reactions. XII. Sterically hindered aliphatic carbonyl compounds. II. Ketones containing the dineopentylcarbinyl group. *J. Am. Chem. Soc.*, 64:1247-1251.

Whitmore, et al. 1947. Higher hydrocarbons. IV. Six phenyleicosanes and six cyclohexyleicosanes. *J. Am. Chem. Soc.*, 69:235-237.

Wolf, V. V. 1952. Über alkin-amine I. Aryl-propargyl-amine. *Liebigs Ann. Chem.*, 576:35-45.

Wolfe, et al. 1996. An improved catalyst system for aromatic carbon-nitrogen bond formation: The possible involvement of bis(phosphine) palladium complexes as key intermediates. *J. Am. Chem. Soc.*, 118:7215-7216.

Yamada, et al. 1998. Alternative synthesis of TTF donors with a dioxolane ring, and synthesis of their dithiolane and oxathiolane analogues. *Tetrahedron Letters*, 39:7709-7712.

Yang, et al. 1999. Palladium-catalyzed amination of aryl halides and sulfonates. *Journal of Organometallic Chemistry*, 576:125-146.

Yasuhara, et al. 2000. An activated phosphate for an efficient amide and peptide coupling reagent. *J. Chem. Soc., Perkin Trans. 1*, 17:2901-2902.

Yin, et al. 2002. Pd-catalyzed intermolecular amidation of aryl halides: The discovery that xantphos can be trans-chelating in a palladium complex. *J. Am. Chem. Soc.*, 124:6043-6048.

Caroon, et al. 1981. Synthesis and antihypertensive activity of a series of 8-substituted 1-Oxa-3,8-diazaspiro[4.5]decan-2-ones. *J. Med. Chem.*, 24:1320-1328.

Chemical Abstracts, 73:25305. Benke, et al. 1970.

Clifton, et al. 1982. Arylethanolamines Derived from Salicylamide with •- and •-Adrenoceptor Blocking Activities. Preparation of Labetalol, its Enantiomers, and Related Salicyclamides. *J. Med. Chem.*, 25:670-679.

Delecluse, et al. 1998. A case of tardive tremor successfully treated with clozapine. *Movement Disorders*, 13(5):846-847.

Dorwald, F.Z., "Side Reactions in Organic Synthesis: A Guide to Successful Synthesis Design" 2005 Wiley-VCH GmbH & KGaA, Wienheim.

Factor, et al. 1992. Clozapine prevents recurrence of psychosis in Parkinson's disease. *Movement Disorders*, 7(2):125-131.

Factor, et al. 2001. Clozapine for the treatment of drug-induced psychosis in Parkinson's disease: Results of the 12 week open label extension in the Psyclops trial. *Movement Disorders*, 16(1):135-139.

Friedman, J. H. 1994. Clozapine treatment of psychosis in patients with tardive dystonia: Report of three cases. *Movement Disorders*, 9(3):321-324.

Harper, et al. 1964. The chemistry and pharmacology of some 4-aminopiperidines and their derivatives. *J. Med. Chem.*, 44:729-732.

Herrick-Davis, et al. 2000. Inverse agonist activity of atypical antipsychotic drugs at human 5-hydroxytryptamine2C receptors. *The Journal of Pharmacology and Experimental Therapeutics*, 295(1):226-232.

Kalgutkar, et al. 1995. Selective inhibitors of monoamine oxidase (MAO-A and MAO-B) as probes of its catalytic site and mechanism. *Medicinal Research Reviews*, 15(4)325-388. XP002034298.

March, et al., Journal of Advanced Organic Chemistry: Reactions, Mechanism and Structure, 5th Edition, p. 423.

Möehrle, et al. 1990. Sodium mercury edetate dehydrogenation of N-aliphatic substituted 1,2,3,6-tetrahydropyridine derivatives. *Arch. Pharm.* (Weinheim), 323:109-115.

Ryckmans, et al. 2002. First dual NK1 antagonists—serotonin reuptake inhibitors: synthesis and SAR of a new class of potential antidepressants. *Biorganic & Medicinal Chemistry Letters* 12:261-264.

Smith, et al. 1995. New spiropiperdines as potent and selective non-peptide tachykinin $NK_2$ receptor antagonists. *J. Med. Chem.*, 38(19):3772-3779.

Thomas, et al. 1997. "Rapid in-plate generationof benzimidazole libraries and amide formation using EEDQ," *Tetrahedron Lett.* 39(29):5099-5102.

Wade, et al. 2000. Application of base cleavable safety catch linkers to solid phase library production. *J. Comb. Chem.*, 2(3):266-275.

Yoshida, et al. 1998. Marked improvement of tardive dystonia after replacing haloperidol with risperidone in a schizophrenic patient. *Clinical Neuropharmacology*, 21(1):68-69.

Notice of Allowance and Fee(s) Due and Notice of Allowability dated May 15, 1997, from U.S. Appl. No. 08/273,669, filed Jul. 12, 1994, now U.S. Pat. No. 5,707,798.

Office Action dated Mar. 27, 1998, from U.S. Appl. No. 08/954,724, filed Oct. 20, 1997, now U.S. Pat. No. 5,912,132.

Notice of Allowance and Fee(s) Due and Notice of Allowability dated Sep. 4, 1998, from U.S. Appl. No. 08/954,724, filed Oct. 20, 1997, now U.S. Pat. No. 5,912,132.

Office Action dated Sep. 14, 1998, from U.S. Appl. No. 08/965,947, filed Nov. 7, 1997, now U.S. Pat. No. 5,955,281.

Interview Summary dated Nov. 17, 1998, from U.S. Appl. No. 08/965,947, filed Nov. 7, 1997, now U.S. Pat. No. 5,955,281.

Office Action dated Apr. 25, 2002, from U.S. Appl. No. 09/800,096, now U.S. Pat. No. 6,815,458.

Office Action dated Jan. 21, 2003, from U.S. Appl. No. 09/800,096, now U.S. Pat. No. 6,815,458.

Office Action dated Jul. 15, 2003, from U.S. Appl. No. 09/800,096, now U.S. Pat. No. 6,815,458.

Notice of Allowability dated Dec. 8, 2003, from U.S. Appl. No. 09/800,096, filed Mar. 6, 2001, now U.S. Pat. No. 6,815,458.

Notice of Allowance and Fee(s) Due and Notice of Allowability dated Dec. 5, 2003, from U.S. Appl. No. 10/409,782, filed Apr. 7, 2003, now U.S. Pat. No. 6,756,393.

International Preliminary Examination Report dated Mar. 18, 2003, for PCT/US01/07187.

International Search Report dated Jul. 17, 2001 for PCT/US01/07187.

Written Opinion dated Nov. 22, 2002 for PCT/US01/07187.

Office Action dated Feb. 28, 2001, from U.S. Appl. No. 09/413,626, filed Oct. 6, 1999, now U.S. Pat. No. 6,358,698.

Notice of Allowance and Fee(s) Due and Notice of Allowability dated Nov. 20, 2001, from U.S. Appl. No. 09/413,626, filed Oct. 6, 1999, now U.S. Pat. No. 6,358,698.

Office Action dated May 21, 2004, from U.S. Appl. No. 10/329,719, filed Dec. 23, 2002, now U.S. Pat. No. 6,911,452.

Notice of Allowance and Fee(s) Due and Notice of Allowability dated Feb. 11, 2005, from U.S. Appl. No. 10/329,719, filed Dec. 23, 2002, now U.S. Pat. No. 6,911,452.

Office Action dated Jan. 17, 2006, from U.S. Appl. No. 11/154,083, filed Jun. 26, 2005.

Office Action dated Jun. 26, 2006, from U.S. Appl. No. 11/154,083, filed Jun. 26, 2005.

Notice of Allowability, Notice of Allowance and Fee(s) Due, and Interview Summary dated Dec. 15, 2006, from U.S. Appl. No. 11/154,083, filed Jun. 16, 2005.

Office Action dated Oct. 5, 2006, from U.S. Appl. No. 11/418,322, filed May 3, 2006.

Office Action dated Jan. 23, 2007, from U.S. Appl. No. 11/418,322, filed May 3, 2006.

International Search Report dated May 8, 2003 for PCT/US02/41476.

Written Opinion dated Sep. 9, 2003, for PCT/US02/41476.

International Preliminary Examination Report dated Jan. 15, 2004, for PCT/US02/41476.

Office Action dated Nov. 4, 2004, from U.S. Appl. No. 10/601,070, filed Jun. 20, 2003.

Notice of Allowance and Fee(s) Due and Notice of Allowability dated Jul. 12, 2005, from U.S. Appl. No. 10/601,070, filed Jun. 20, 2003.

Notice of Allowance and Fee(s) Due and Notice of Allowability dated Mar. 29, 2006, from U.S. Appl. No. 10/601,070, filed Jun. 20, 2003.

International Search Report dated Dec. 3, 2003, for PCT/US03/19797.

Written Opinion for PCT/US03/19797 dated Apr. 5, 2004.

International Preliminary Examination Report dated Jul. 28, 2004 for PCT/US03/19797.

International Search Report dated Sep. 8, 2004, for PCT/US2004/001234.

International Written Opinion dated Sep. 8, 2004, for PCT/US2004/001234.

International Preliminary Report on Patentability dated Apr. 14, 2005, for PCT/US2004/001234.

International Search Report dated Jan. 30, 2006, for PCT/US2005/034813.

Written Opinion of the International Searching Authority dated Jan. 30, 2006, for PCT/US2005/034813.

International Search Report dated Jan. 30, 2006, for PCT/US2005/034376.
Written Opinion of the International Searching Authority dated Jan. 30, 2006, for PCT/US2005/034376.
International Preliminary Report on Patentability dated Mar. 27, 2007, for PCT/US2005/034376.
International Preliminary Report on Patentability dated Mar. 27, 2007, for PCT/US2005/034813.
Office Action dated Apr. 6, 2007, from U.S. Appl. No. 11/418,322, filed May 3, 2006.
Office Action dated May 8, 2007, from U.S. Appl. No. 11/417,866, filed May 3, 2006.
Notice of Allowance and Fee(s) Due and Notice of Allowability dated Mar. 5, 2007, from U.S. Appl. No. 10/601,070, filed Jun. 20, 2003.
Office Action dated Feb. 5, 2007, from U.S. Appl. No. 11/299,566, filed Dec. 12, 2005.
Notice of Allowance and Fee(s) Due and Notice of Allowability dated Jun. 19, 2007, from U.S. Appl. No. 11/418,322, filed May 3, 2006.
Office Action dated Oct. 22, 2007 from U.S. Appl. No. 11/417,782, filed May 3, 2006.
Office Action dated Oct. 12, 2007 from U.S. Appl. No. 11/417,439, filed May 3, 2006.
Office Action dated Oct. 2, 2007, from U.S. Appl. No. 11/299,566, filed Dec. 12, 2005.
Office Action dated Oct. 26, 2007, from U.S. Appl. No. 11/417,866, filed May 3, 2006.
Office Action dated Oct. 10, 2007, from U.S. Appl. No. 10/759,561, filed Jan. 15, 2004.
Office Action dated Jan. 30, 2008, from U.S. Appl. No. 11/417,790, filed May 3, 2006.
Office Action dated Jan. 25, 2008, from U.S. Appl. No. 10/802,970, filed Mar. 16, 2004.
Notice of Allowance and Fee(s) Due and Notice of Allowability dated Feb. 19, 2008, from U.S. Appl. No. 11/417,439, filed May 3, 2006.
Office Action dated Dec. 17, 2007, from U.S. Appl. No. 11/299,566, filed Dec. 12, 2005.
Office Action dated Feb. 22, 2008, from U.S. Appl. No. 11/417,866, filed May 3, 2006.
Office Action dated Mar. 28, 2008, from U.S. Appl. No. 11/417,782, filed May 3, 2006.
Office Action dated Jul. 14, 2006, from U.S. Appl. No. 10/601,070, filed Jun. 20, 2003.
Supplemental Notice of Allowability dated May 23, 2008, from U.S. Appl. No. 11/417,439, filed May 3, 2006.
Office Action dated Jun. 2, 2008, from U.S. Appl. No. 11/687,552, filed Mar. 16, 2007.
Office Action dated Jul. 17, 2008, from U.S. Appl. No. 10/802,970, filed Mar. 16, 2004.
Notice of Allowance and Fee(s) Due and Notice of Allowability dated Jul. 23, 2008, from U.S. Appl. No. 11/299,566, filed Dec. 12, 2005.
Notice of Allowance and Fee(s) Due and Notice of Allowability dated Sep. 9, 2008, from U.S. Appl. No. 11/417,866, filed May 3, 2006.
Notice of Allowance and Fee(s) Due and Notice of Allowability dated Oct. 28, 2008, from U.S. Appl. No. 11/687,552, filed Mar. 16, 2007.
Nakanishi, et al. 1971. Studies on piperidine derivatives. 3. Studies on the synthesis of 3-oxo-1-thia-4,8-diazaspiro [4,5] decane derivatives. (1). J. of the Pharmaceutical Society of Japan, 91(3):363-383.
Office Action dated Aug. 13, 2009 from U.S. Appl. No. 11/418,353, filed May 3, 2006.

SPIROAZACYCLIC COMPOUNDS AS MONOAMINE RECEPTOR MODULATORS

RELATED APPLICATIONS

The present application is a continuation of and claims priority to U.S. patent application Ser. No. 11/687,552, filed Mar. 16, 2007, by Schlienger, entitled "SPIROAZACYCLIC COMPOUNDS AS MONOAMINE RECEPTOR MODULATORS," which is a continuation of and claims priority to U.S. patent application Ser. No. 11/154,083, now U.S. Pat. No. 7,217,719, filed on Jun. 16, 2005, by Schlienger, entitled "SPIROAZACYCLIC COMPOUNDS AS MONOAMINE RECEPTOR MODULATORS," which is a divisional application of and claims priority to U.S. patent application Ser. No. 10/329,719, now U.S. Pat. No. 6,911,452, filed on Dec. 23, 2002 by Schlienger, entitled "SPIROAZACYCLIC COMPOUNDS AS MONOAMINE RECEPTOR MODULATORS," which claims priority to U.S. Provisional Application Ser. No. 60/344,750, filed Dec. 28, 2001 by Schlienger, entitled "SPIROAZACYCLIC COMPOUNDS AS MONOAMINE RECEPTOR MODULATORS," all of which are incorporated by reference herein in their entirety, including any drawings and claims as originally filed.

FIELD OF INVENTION

The present invention relates to novel compounds that affect monoamine receptors, including serotonin receptors. The invention specifically provides compounds that are active as inverse agonists, and therefore also as antagonists, at the 5-HT2A subtype of human serotonin receptors. The invention also provides methods, utilising the compounds of the invention for modulating 5-HT2A receptor-mediated events that are useful for treating or alleviating disease conditions in which modification of the activity of these receptors is beneficial.

BACKGROUND

Serotonin or 5-hydroxytryptamine (5-HT) plays a significant role in the functioning of the mammalian body. In the central nervous system, 5-HT is an important neurotransmitter and neuromodulator that is 11 implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neurol.* 150:3-15, (1994)). Peripheral functions in the cardiovascular, hematological and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission*, 1982; Boullin, *Serotonin In Mental Abnormalities* 1:316 (1978); Barchas, et al., *Serotonin and Behavior*, (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis. Given the broad distribution of serotonin within the body, tremendous interest in drugs that affect serotonergic systems exists (Gershon, et al., *The Peripheral Actions of 5-Hydroxytryptamine*, 246 (1989); Saxena, et al., *J. Cardiovascular Pharmacol.* 15: Supp. 7 (1990)).

Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s).

Serotonin may be an important component in various types of pathological conditions such as psychiatric disorders (depression, aggressiveness, panic attacks, obsessive compulsive disorders, psychosis, schizophrenia, suicidal tendency), neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology*, 21:106 S-115S (1999); Barnes & Sharp, *Neuropharmacology*, 38:1083-1152 (1999); Glennon, *Neurosci. Biobehavioral Rev.*, 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus, there is a need to develop drugs that are selective for individual receptor classes and subclasses amongst monoaminergic neurotransmitter receptors.

One theory for the mechanism of action of antipsychotic drugs involves antagonism of dopamine D2 receptors. Unfortunately, it is likely that antagonism of dopamine D2 receptors also mediates the extrapyramidal side effects. Antagonism of 5-HT2A is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they can activate or inactivate these molecules, respectively. In contrast, classic or neutral antagonists compete against agonists and inverse agonists for access to the receptor, but do not possess the intrinsic ability to inhibit elevated basal or constitutive receptor responses.

We have recently elucidated an important aspect of 5-HT2A receptor function by applying the Receptor Selection and Amplification Technology (U.S. Pat. No. 5,707,798, 1998; *Chem. Abstr.* 128:111548 (1998) and citations therein), to the study of the 5-HT2 subclass of serotonin receptors. R-SAT is a phenotypic assay of receptor function that involves the heterologous expression of receptors in mammalian fibroblasts. Using this technology we were able to demonstrate that native 5-HT2A receptors possess significant constitutive, or agonist-independent, receptor activity (Weiner et. al. *J. Pharmacol. Exp. Ther.* 2001, 299 (1), 268-276.). Furthermore, by directly testing a large number of centrally acting medicinal compounds with known clinical activity in neuropsychiatric disease, we determined that compounds with antipsychotic efficacy all shared a common molecular property. Nearly all of these compounds, which are used by psychiatrists to treat psychosis, were found to be potent 5-HT2A inverse agonists. This unique clinico-pharmacologic correlation at a single receptor subtype is compelling evidence that 5-HT2A receptor inverse agonism is a molecular mechanism of antipsychotic efficacy in humans.

Detailed pharmacological characterization of a large number of antipsychotic compounds revealed that they possess broad activity at multiple related receptor subtypes. Most of these compounds display agonist, competitive antagonist, or inverse agonist activity at multiple monoaminergic receptor subtypes, including serotoninergic, dopaminergic, adrenergic, muscarinic and histaminergic receptors. This broad activity is likely responsible for the sedating, hypotensive, and motor side effects of these compounds. It would therefore be of great advantage to develop compounds that are selective inverse agonists of the 5-HT2A receptor, but which have little or no activity on other monamine receptor subtypes, especially dopamine D2 receptors. Such compounds may be useful in the treatment of human disease (e.g., as anti-psychotics), and may avoid the adverse side effects associated with non-selective receptor interactions.

U.S. Pat. No. 4,853,394 describes non-spirocyclic piperidyl esters and amides not within the scope of the compounds of formula I.

Smith et al (*J. Med. Chem*, 1995, 38, 3772) describes spiropiperidines including oxazolidinones, hydantoins, imidazolidinones, pyrrolidinones, pyrazolidonones and pyrrolidines not within the scope of the compounds of formula I.

Maunkel et al (*J. Med Chem*, 1996, 39, 3169) describes pseudopeptide badykinin B2 receptor antagonists containing 1,3,8-triaza[4.5]decan-4-one ring systems not within the scope of the compounds of formula I.

Strosberg et al (*J. Med Chem*, 1981, 24, 1320) describes 1-oxa-3,8-diazaspiro[4.5]decan-2-ones not within the scope of the compounds of formula I.

Strosberg et al (*J. Med Chem*, 1983, 27, 855) describes 9-substituted 1-oxa-4,9-diazaspiro[5.5]undecan-3-ones not within the scope of the compounds of formula I.

Tsukamoto et al (*Chem. Pharm. Bull*, 1995, 43(9), 1523) describes 1-oxa-2,8-diazaspiro[4.5]decan-3-ones as $M_1$ muscarinic agonists. However, none of the compounds of Tsukamoto et al are within the scope of the compounds of formula I and the compounds of Tsukamoto et al do not relate to the methods of the invention.

WO 97/11940 describes compounds as inhibitors of fibrinogen-dependent platelet aggregation not within the scope of the compounds of formula I.

Weiner et. al. (*J. Pharmacol. Exp. Ther.* 2001, 299 (1), 268-276) describes 5-HT2A inverse agonists not within the scope of the compounds of formula I.

PCT/US01/07187 describes non-spirocyclic N-(4-piperidinyl) dibenzyl amides and ureas not within the scope of the compounds of formula I.

U.S. Pat. No. 6,150,393, U.S. Pat. No. 6,140,509, U.S. Pat. No. 6,107,324 and EP1071701, describes non-spirocyclic compounds not within the scope of the compounds of formula I.

WO99/52927 describes non-spirocyclic phenyl pyrazole derivatives not within the scope of the compounds of formula I.

SUMMARY OF THE INVENTION

The invention provides compounds of formula I, salts and stereoisomers thereof

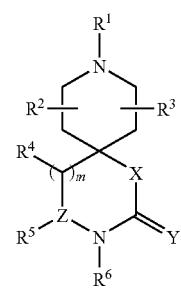

wherein X is selected from the group consisting of $CH_2$, $CH_2CH_2$, $CH_2O$, $OCH_2$, O, $CH_2S$, $SCH_2$, S, $CH_2N(R^N)$, $N(R^N)CH_2$ and $N(R^N)$; wherein $R^N$ is selected from hydrogen and $C_{1-6}$ alkyl;

Y is selected from the group consisting of O and S;

Z is absent or selected from the group consisting of CH and N;

$R^1$ is selected from the group consisting of hydrogen, optionally substituted $C_{1-6}$ alkyl, $C_{2-8}$ alkenyl, $C_{2-8}$ alkynyl, optionally substituted $C_{3-6}$ cycloalkyl, aryl, and heteroaryl;

m is selected from the group consisting of 0 and 1;

$R^4$, $R^5$, and $R^6$ are independently selected from the group consisting of hydrogen, $C_{1-6}$ alkyl, aryl($C_{1-6}$ alkyl), heteroaryl($C_{1-6}$ alkyl), heterocyclyl($C_{1-6}$ alkyl), hydroxy($C_{1-6}$ alkyl), amino($C_{1-6}$ alkyl), halo($C_{1-6}$ alkyl), optionally substituted $C_{3-6}$ cylcoalkyl, aryl, and heteroaryl, wherein at least two of $R^4$, $R^5$, and $R^6$ are independently selected from the group consisting of aryl($C_{1-6}$ alkyl), heteroaryl($C_{1-6}$ alkyl), and heterocyclyl($C_{1-6}$ alkyl);

$R^2$ and $R^3$ are independently selected from the group consisting of hydrogen, halogen, hydroxy, and optionally substituted $C_{1-6}$ alkyl or selected such that $R^2$ and $R^3$ together form a ring system such that

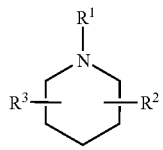

is selected from the group consisting of

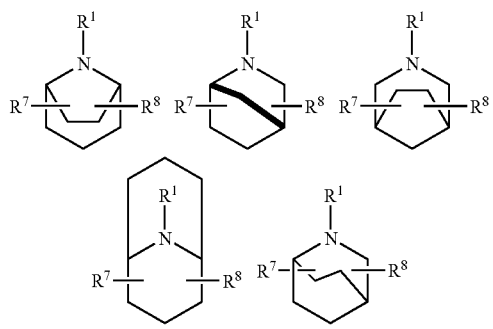

wherein $R^7$ and $R^8$ are independently selected from the group consisting of hydrogen, halogen, hydroxy, and $C_{1-6}$ alkyl.

The invention also provides pharmaceutical compositions including invention compounds. In one embodiment, a composition includes a compound of formula I, a pharmaceutically acceptable salt thereof or a stereoisomer, together with a pharmaceutically acceptable carrier or excipient.

The invention further provides methods of inhibiting an activity or activation of a monoamine receptor. In one embodiment, a method includes contacting a monoamine receptor or a system containing a monoamine receptor with an effective amount of one or more of the compounds of formula I to inhibit an activity of the monoamine receptor. In another embodiment, a method includes contacting a monoamine receptor or a system containing a monoamine receptor with an effective amount of one or more of the compounds of formula I to inhibit activation of the monoamine receptor.

The invention additionally provides methods of treating a disease condition associated with a monoamine receptor. In one embodiment, a method includes administering to a subject in need of such treatment a therapeutically effective amount of one or more of the compounds of formula I. In various aspects, the disease condition is selected from the group consisting of schizophrenia, psychosis, migraine, hypertension, thrombosis, vasospasm, ischemia, depression, anxiety, sleep disorders and appetite disorders.

Further provided are uses of a compound of formula I for the preparation of a medicament for the treatment of a disease condition. In one embodiment, a use of a compound of formula I for the preparation of a medicament is for treatment of a disease condition associated with a monoamine receptor. In various aspects, the disease condition is selected from the group consisting of schizophrenia, psychosis, migraine, hypertension, thrombosis, vasospasm, ischemia, depression, anxiety, sleep disorders and appetite disorders.

Still further, the invention provides methods for identifying a genetic polymorphism predisposing a subject to being responsive to one or more compounds of formula I. In one embodiment, a method includes:

administering to a subject a therapeutically effective amount of the compound;

measuring the response of said subject to said compound, thereby identifying a responsive subject having an ameliorated disease condition associated with a monoamine receptor; and identifying a genetic polymorphism in the responsive subject, wherein the genetic polymorphism predisposes a subject to being responsive to the compound.

In an additional aspect, the invention provides methods for identifying a subject suitable for treatment with one or more of the compounds formula I. In one embodiment, a method includes detecting the presence of a polymorphism in a subject wherein the polymorphism predisposes the subject to being responsive to the compound, and wherein the presence of the polymorphism indicates that the subject is suitable for treatment with one or more of the compounds of formula I.

The invention provides kits including one or more compounds of the invention, and instructions for practicing a method of the invention. In one embodiment, instructions are for methods of inhibiting an activity or activation of a monoamine receptor. In another embodiment, instructions are for treating a disease condition associated with a monoamine receptor. In still another embodiment, instructions are for administering to a subject in need of such treatment a therapeutically effective amount of one or more of the compounds of formula I. In various aspects, the subject has or is at risk of having schizophrenia, psychosis, migraine, hypertension, thrombosis, vasospasm, ischemia, depression, anxiety, sleep disorder or an appetite disorder.

BRIEF DESCRIPTION OF THE DRAWING FIGURES

DESCRIPTION OF THE INVENTION

Figure 1:
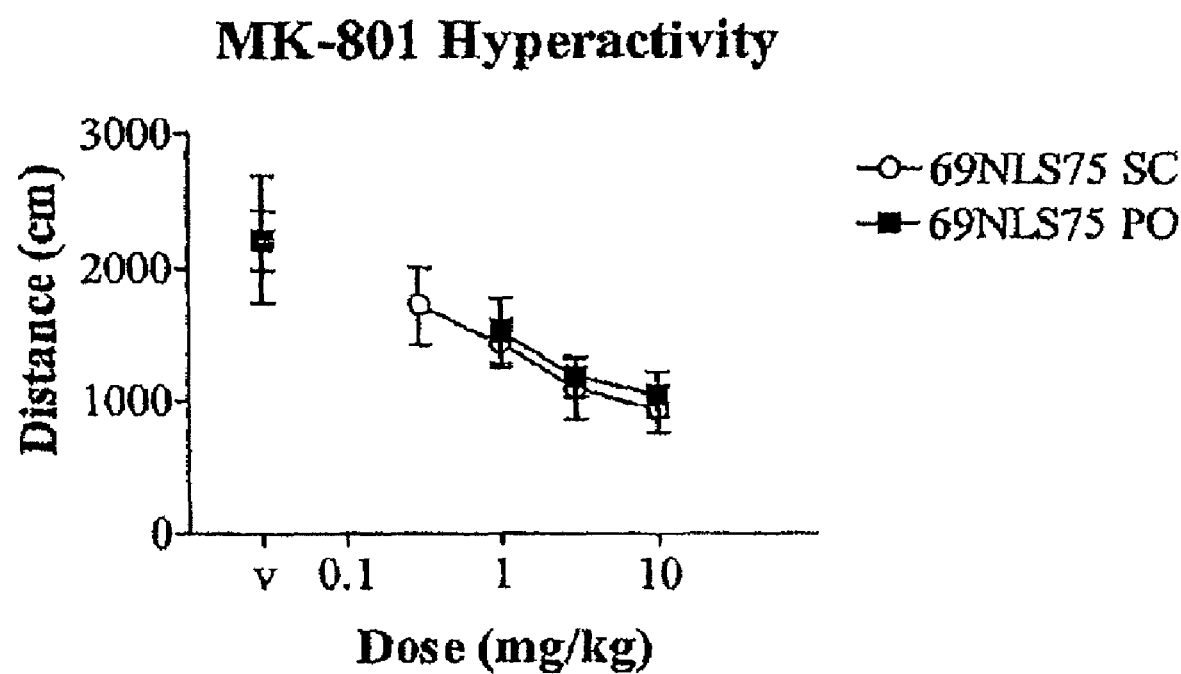
FIG. 1 shows the effect of 69NLS75 on hyperactivity in mice treated with MK-801.
Figure 2:
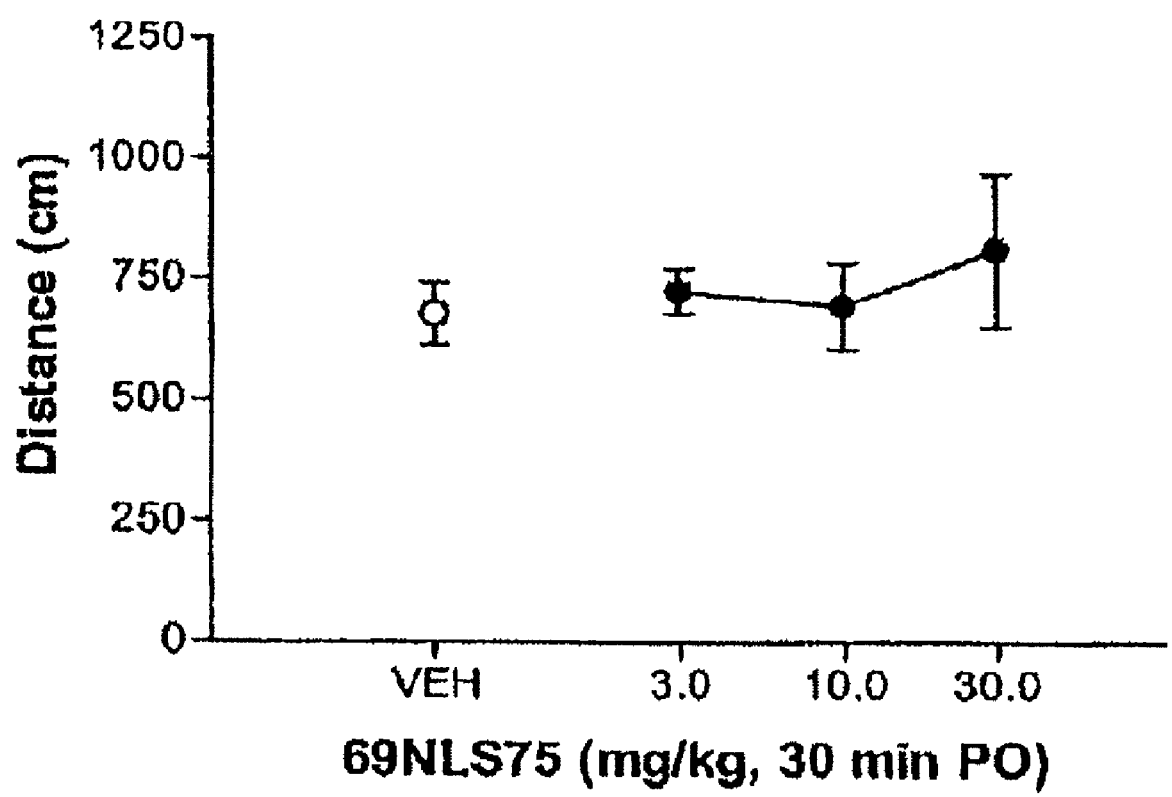
FIG. 2 shows the dose effect of 69 NLS75 on spontanteous locomotor activity.

For the purpose of the current disclosure, the following definitions shall in their entireties be used to define technical terms. The term "Constitutive activity" is defined as the elevated basal activity of a receptor, which is independent of the presence of an agonist. Constitutive activity of a receptor may be measured using a number of different methods, including cellular (e.g., membrane) preparations (see, e.g., Barr &. Manning, *J. Biol. Chem.* 272:32979-87 (1997)), purified reconstituted receptors with or without the associated G-protein in phospholipid vesicles (Cerione et al., *Biochemistry* 23:4519-25 (1984)), and functional cellular assays (U.S. patent application Ser. No. 09/413,626).

The term "agonist" is defined as a compound that increases the activity of a receptor when it contacts the receptor.

The term "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity.

The term "inverse agonist" is defined as a compound that decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The term "5-HT2A receptor" is defined as a receptor, having an activity corresponding to the activity of the human serotonin receptor subtype, which was characterized through molecular cloning and pharmacology as detailed in Saltzman et al., *Biochem. Biophys. Res. Comm.* 181:1469-78; and Julius et al., *Proc. Natl. Acad. Sci. USA* 87:928-932.

The term "subject" refers to an animal, such as a mammal, for example, a human, who is the object of treatment, observation or experiment.

The term "selective" is defined as a property of a compound whereby an amount of the compound sufficient to effect a desired response from a particular receptor type, subtype, class or subclass causes a substantially smaller or no effect upon the activity other receptor types.

The terms "selectivity" or "selective," in relation to an inverse agonist, are understood as a property of a compound whereby an amount of compound that effectively inversely agonizes the 5-HT2A receptor, and thereby decreases its activity, causes little or no inverse agonistic or antagonistic activity at other, related or unrelated, receptors. In particular, the compounds of the invention have surprisingly been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. The compounds of the invention can also be selective with respect to other monoamine-binding receptors, such as the dopaminergic, histaminergic, adrenergic and muscarinic receptors. Compounds that are highly selective for 5-HT2A receptors may have a beneficial effect in the treatment of psychosis, schizophrenia or similar neuropsychiatric disorders, while avoiding adverse effects associated with other drugs.

The $EC_{50}$ for an agonist is intended to denote the concentration of a compound needed to achieve 50% of a maximal response seen in R-SAT. For inverse agonists, EC50 is intended to denote the concentration of a compound needed to achieve 50% inhibition of an R-SAT response from basal, no compound, levels.

As used herein, the term "coadministration" refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other.

In the present context, the term "$C_{1-6}$-alkyl" means a linear or branched saturated hydrocarbon chain wherein the longest chain has from one to six carbon atoms, such as methyl, ethyl, n-propyl, isopropyl, n-butyl, isobutyl, sec-butyl, tert-butyl, pentyl, isopentyl, neopentyl, and hexyl.

In the present context, the term "$C_{2-8}$-alkenyl" means a linear or branched hydrocarbon group having from two to eight carbon atoms and containing one or more double bonds. Illustrative examples of $C_{2-8}$-alkenyl groups include allyl, homo-allyl, vinyl, crotyl, butenyl, pentenyl, hexenyl, heptenyl and octenyl. Illustrative examples of $C_{2-8}$-alkenyl groups with more than one double bond include butadienyl, pentadienyl, hexadienyl, heptadienyl, heptatrienyl and octatrienyl groups as well as branched forms of these. The position of the unsaturation (the double bond) may be at any position along the carbon chain.

In the present context the term "$C_{2-8}$-alkynyl" means a linear or branched hydrocarbon group containing from two to eight carbon atoms and containing one or more triple bonds. Illustrative examples of $C_{2-8}$-alkynyl groups include ethynyl, propynyl, butynyl, pentynyl, hexynyl, heptynyl and octynyl groups as well as branched forms of these. The position of unsaturation (the triple bond) may be at any position along the carbon chain. More than one bond may be unsaturated such that the "$C_{2-8}$-alkynyl" is a di-yne or enedi-yne as is known to the person skilled in the art.

The terms "haloalkyl", "hydroxyalkyl" and "aminoalkyl" are intended to cover $C_{1-6}$-alkyl groups, defined above, carrying at least one halogen, hydroxy group, or amino group, respectively.

In the present context the term "lower alkylene" means a bivalent hydrocarbon tether, containing from one to six carbon atoms. Additionally, "lower alkylene" tethers may optionally contain one or more substituents selected from $C_{1-6}$ alkyl, halogen, hydroxyl, and amino. Non-limiting examples of "lower alkylene" groups are methylene, ethylene, propylene, tetramethylene, hexamethylene.

In the present context, the term "$C_{3-8}$-cycloalkyl" includes three-, four-, five-, six-, seven-, and eight-membered rings comprising carbon atoms only, whereas the term "heterocyclyl" means three-, four-, five-, six-, seven-, and eight-membered rings wherein carbon atoms together with from 1 to 3 heteroatoms constitute said ring. The heteroatoms of such heterocyclyl groups are independently selected from oxygen, sulphur, and nitrogen.

The term "Heterocyclyl" groups may further contain one or more carbonyl or thiocarbonyl functionalities, so as to make the definition include oxo-systems and thio-systems such as lactams, lactones, cyclic imides, cyclic thioimides, cyclic carbamates, and the like.

$C_{3-8}$-cycloalkyl and heterocyclyl rings may optionally contain one or more unsaturated bonds situated in such a way, however, that an aromatic π-electron system does not arise.

Heterocyclyl rings may optionally also be fused to aryl rings, such that the definition includes bicyclic structures. Such fused heterocyclyl groups can share one bond with an optionally substituted benzene ring. Examples of benzo-fused heterocyclyl groups include, but are not limited to, benzimidazolidinone, tetrahydroquinoline, and methylenedioxybenzene ring structures.

Illustrative examples of "$C_{3-8}$-cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene and 1,3,5 cycloheptatriene.

Illustrative examples of "heterocyclyls" are the heterocycles tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, thiazoline, thiazolidine, 1,3-oxathiolane. Binding to the heterocycle may be at the position of a heteroatom or via a carbon atom of the heterocycle, or, for benzo-fused derivatives, via a carbon of the benzenoid ring.

In the present context the term "aryl" means a carbocyclic aromatic ring or ring system. Moreover, the term "aryl" includes fused ring systems wherein at least two aryl rings, or at least one aryl and at least one $C_{3-8}$-cycloalkyl share at least one chemical bond. Illustrative examples of "aryl" rings include optionally substituted phenyl, naphthalenyl, phenanthrenyl, anthracenyl, tetralinyl, fluorenyl, indenyl, and indanyl. Another aryl group example is phenyl. The term "aryl" relates to aromatic, such as benzenoid groups connected via one of the ring-forming carbon atoms, and optionally carrying one or more substituents selected from halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. As stated, aryl groups may be phenyl, which includes substituted phenyl groups, carrying one or two, same or different, of the substituents listed above. A particular example of a pattern of substitution is para and/or meta. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 3-cyanophenyl, 4-cyanophenyl, dimethylphenyl, naphthyl, hydroxynaphthyl, hydroxymethylphenyl, trifluoromethylphenyl, alkoxyphenyl.

In the present context, the term "heteroaryl" means a heterocyclic aromatic group where one or more carbon atoms in an aromatic ring have been replaced with one or more heteroatoms selected from the group comprising nitrogen, sulphur, phosphorous and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one $C_{3-8}$-cycloalkyl ring share at least one chemical bond.

The term "heteroaryl" is understood to relate to aromatic, $C_{2-6}$ cyclic groups further containing one O or S atom or up to four N atoms, or a combination of one O or S atom with up to two N atoms, and their substituted as well as benzo- and pyrido-fused derivatives, typically connected via one of the ring-forming carbon atoms. Heteroaryl groups may carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Particular heteroaryl groups are five- and six-membered aromatic heterocyclic systems carrying 0, 1, or 2 substituents, which may be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, and tetrazole, as well as furazan, 1,2,3-oxadiazole, 1,2,3-thiadiazole, 1,2,4-thiadiazole, triazole, benzotriazole, quionoline, isoquinoline, pyridazine, pyrimidine, purine, pyrazine, pteridine, pyrrole, phenoxazole, oxazole, isoxazole, oxadiazole, benzopyrazole, indazole, quinolizine, cinnoline, phthalazine, quinazoline, and quinoxaline. The most likely substituents are halo, hydroxy, cyano, O—$C_{1-6}$-alkyl, $C_{1-6}$-alkyl, hydroxy-$C_{1-6}$-alkyl, amino-$C_{1-6}$-alkyl.

The term "aryl($C_{1-6}$-alkyl)" are aryl groups connected, as substituents, via a lower alkylene, each as defined supra. The aryl groups of "aryl($C_{1-6}$-alkyl)" may be substituted or unsubstituted. Examples include benzyl, substituted benzyl, 2-phenylethyl, 3-phenylpropyl, and naphthylalkyl.

The term "heteroaryl($C_{1-6}$-alkyl)" are understood as heteroaryl groups connected, as substituents, via a lower alkylene, each as defined supra. The heteroaryl groups of heteroaralkyl groups may be substituted or unsubstituted. Examples include 2-thienylmethyl, 3-thienylmethyl, furylmethyl, thienylethyl, pyrrolylalkyl, pyridylalkyl, isoxazolylalkyl, imidazolylalkyl, and their substituted as well as benzo-fused analogs.

The term "heterocyclyl($C_{1-6}$-alkyl)" are understood as heterocyclyl groups connected, as substituents, via a lower alkylene, each as defined supra.

The term "cycloalkyl($C_{1-6}$-alkyl)" are understood as cycloalkyl groups connected, as substituents, via a lower alkylene, each as defined supra.

When used herein, the term "O—$C_{1-6}$-alkyl" means $C_{1-6}$-alkyloxy, or alkoxy, such as methoxy, ethoxy, n-propoxy, isopropoxy, n-butoxy, isobutoxy, sec-butoxy, tert-butoxy, pentyloxy, isopentyloxy, neopentyloxy and hexyloxy. Further, the definition of "O—$C_{1-6}$-alkyl" is intended to cover cyclic alkoxy groups having a maximum of six carbon atoms. Illustrative non-limiting examples of cyclic alkoxy groups include cyclobutyloxy, cyclopropylmethyloxy, cyclohexyloxy, and the like.

The term "halogen" includes fluorine, chlorine, bromine and iodine.

In the present context, i.e. in connection with the terms "$C_{1-6}$-alkyl", "aryl", "heteroaryl", "heterocyclyl", "heteroaryl($C_{1-6}$-alkyl)", "aryl($C_{1-6}$-alkyl)", "cycloalkyl($C_{1-6}$-alkyl)", "$C_{3-8}$-cycloalkyl", "heterocyclyl($C_{1-6}$-alkyl)", "O—$C_{1-6}$-alkyl", "$C_{2-8}$-alkenyl", and "$C_{2-8}$-alkynyl", the term "optionally substituted" means that the group in question may be substituted one or several times, such as 1 to 5 times, 1 to 3 times, or 1 to 2 times, with one or more groups selected from $C_{1-6}$-alkyl, $C_{1-6}$-alkoxy, oxo (which may be represented in the tautomeric enol form), carboxyl, amino, hydroxy (which when present in an enol system may be represented in the tautomeric keto form), nitro, alkylsulfonyl, alkylsulfenyl, alkylsulfinyl, $C_{1-6}$-alkoxycarbonyl, $C_{1-6}$-alkylcarbonyl, formyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, and halo. In general, the above substituents may be susceptible to further optional substitution.

The term homochiral should be interpreted according to the definition in "Principles of Asymmetric Synthesis" (Gawley and Aubé, Pergamon, 1996, ISBN 0 08 0418759).

The term "salt" means pharmaceutically acceptable acid addition salts obtainable by treating the base form of a functional group, such as an amine, with appropriate acids such as inorganic acids, for example hydrohalic acids; typically hydrochloric, hydrobromic, hydrofluoric, or hydroiodic acid; sulfuric acid; nitric acid; phosphoric acid and the like; or organic acids, for example acetic, propionic, hydroacetic, 2-hydroxypropanoic acid, 2-oxopropanoic acid, ethandioic, propanedioic, butanedioic, (Z)-2-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic acid, cyclohexanesulfamic, 2-hydroxybenzoic, 4-amino-2-hydroxybenzoic, and other acids known to the skilled practitioner.

The invention provides compounds, a subset of which show a relatively high selectivity toward serotonin receptors, particularly, 5-HT2A receptors, which may have a beneficial effect in the treatment of neuropsychiatric disorders.

In a preferred embodiment, compounds of the present invention are defined by formula I, and include salts and stereoisomers thereof, as well as pharmaceutical compositions

I

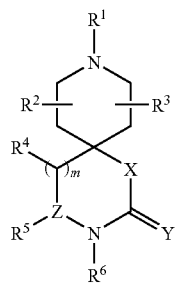

wherein X is selected from the group consisting of $CH_2$, $CH_2CH_2$, $CH_2O$, $OCH_2$, O, $CH_2S$, $SCH_2$, S, $CH_2N(R^N)$, $N(R^N)CH_2$ and $N(R^N)$; wherein $R^N$ is selected from hydrogen and $C_{1-6}$ alkyl;

Y is selected from the group consisting of O and S;

Z is absent or selected from the group consisting of CH and N;

$R^1$ is selected from the group consisting of hydrogen, optionally substituted $C_{1-6}$ alkyl, $C_{2-8}$ alkenyl, $C_{2-8}$ alkynyl, optionally substituted $C_{3-6}$ cycloalkyl, aryl, and heteroaryl;

m is selected from the group consisting of 0 and 1;

$R^4$, $R^5$, and $R^6$ are independently selected from the group consisting of hydrogen, $C_{1-6}$ alkyl, aryl($C_{1-6}$ alkyl), heteroaryl($C_{1-6}$ alkyl), heterocyclyl($C_{1-6}$ alkyl), hydroxy($C_{1-6}$ alkyl), amino($C_{1-6}$ alkyl), halo($C_{1-6}$ alkyl), optionally substituted $C_{3-6}$ cylcoalkyl, aryl, and heteroaryl, wherein at least two of $R^4$, $R^5$, and $R^6$ are independently selected from the group consisting of aryl($C_{1-6}$ alkyl), heteroaryl($C_{1-6}$ alkyl), and heterocyclyl($C_{1-6}$ alkyl);

$R^2$ and $R^3$ are independently selected from the group consisting of hydrogen, halogen, hydroxy, and optionally substituted $C_{1-6}$ alkyl or selected such that $R^2$ and $R^3$ together form a ring system such that

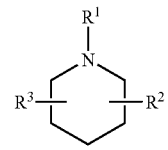

is selected from the group consisting of

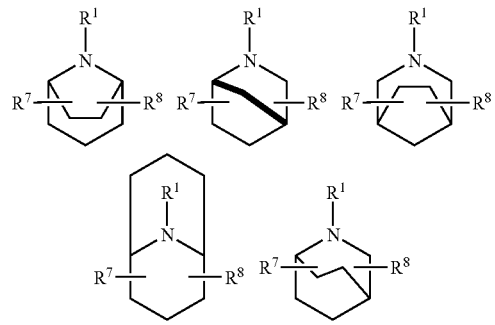

wherein $R^7$ and $R^8$ are independently selected from the group consisting of hydrogen, halogen, hydroxy, and $C_{1-6}$ alkyl.

The compounds of formula I exhibit activity at monoamine receptors, specifically serotonin receptors. Certain compounds share the common property of acting as inverse agonists at the 5-HT2A receptor. Thus, experiments performed on cells transiently expressing the human phenotype of said receptor have shown that the compounds of general formula (I) attenuate the signaling of such receptors in the absence of additional ligands acting upon the receptor. The compounds have thus been found to possess intrinsic activity at this receptor and are able to attenuate the basal, non-agonist-stimulated, constitutive signaling responses that the 5-HT2A receptor displays. The observation that the compounds of general formula (I) are inverse agonists also indicates that these compounds have the ability to antagonize the activation of 5-HT2A receptors that is mediated by endogenous agonists or exogenous synthetic agonist ligands.

The invention therefore provides compounds of formula I, salts and stereoisomers thereof, including compounds that show a relatively high degree of selectivity towards the 5-HT2A subtype of serotonin receptors relative to other subtypes of the serotonin (5-HT) family of receptors as well as to other receptors, most particularly the monoaminergic G-protein coupled receptors, such as dopamine receptors. In one embodiment, the compounds of the invention act as inverse agonists at the 5-HT2A subtype of serotonin receptors.

The compounds of general formula (I) may therefore be useful for treating or alleviating symptoms of disease conditions associated with impaired function, in particular elevated levels of activity, of especially 5-HT2A receptors, whether this impaired function is associated with improper levels of receptor stimulation or phenotypical aberrations.

Others have previously hypothesised that certain neuropsychological diseases might be caused by altered levels of constitutive activity of monoamine receptors. Such constitutive activity might be modified via contacting the relevant receptor with a synthetic inverse agonist. By directly testing a large number of centrally acting medicinal compounds with known clinical activity in neuropsychiatric disease, compounds with antipsychotic efficacy all shared a common molecular property. Nearly all of these compounds that are used by psychiatrists to treat psychosis were found to be potent 5-HT2A inverse agonists. This correlation is compelling evidence that 5-HT2A receptor inverse agonism is a molecular mechanism of antipsychotic efficacy in humans.

Detailed pharmacological characterization of a large number of antipsychotic compounds in our laboratory revealed that they possess broad activity at multiple related receptor subtypes. Most of these compounds display either agonist, competitive antagonist, or inverse agonist activity at multiple monoaminergic receptor subtypes including serotoninergic, dopaminergic, adrenergic, muscarinic and histaminergic receptors. This broad activity is likely responsible for the sedating, hypotensive, and motor side effects of these compounds. It therefore follows that the compounds disclosed herein will possess efficacy as, for example, novel antipsychotics, but will have fewer or less severe side effects than existing compounds.

The present invention is also directed to pharmaceutical compositions comprising a compound of general formula I.

Within this embodiment, at least two of $R^4$, $R^5$, and $R^6$ may be independently selected from the group consisting of 4-monosubstituted-aryl($C_{1-6}$ alkyl), and 4-monosubstituted-heteroaryl($C_{1-6}$ alkyl).

Typically, at least one of the at least two of $R^4$, $R^5$, and $R^6$ independently selected from the group consisting of aryl($C_{1-6}$ alkyl) and heteroaryl($C_{1-6}$ alkyl) is selected from the group consisting of fluoro-substituted-aryl($C_{1-6}$ alkyl), and fluoro-substituted-heteroaryl($C_{1-6}$ alkyl). Also typically, the other of the at least two of $R^4$, $R^5$, and $R^6$ independently selected from the group consisting of aryl($C_{1-6}$ alkyl) and heteroaryl($C_{1-6}$ alkyl) is selected from the group consisting of (O—$C_{1-6}$ alkyl)-substituted-aryl($C_{1-6}$ alkyl), and (O—$C_{1-6}$ alkyl)-substituted-heteroaryl($C_{1-6}$ alkyl).

In some embodiments, at least one of $R^4$, $R^5$, and $R^6$ is selected from the group consisting of fluoro-substituted-aryl ($C_{1-6}$ alkyl), and fluoro-substituted-heteroaryl($C_{1-6}$ alkyl).

Typically, the at least two of $R^4$, $R^5$, and $R^6$ independently selected from the group consisting of aryl($C_{1-6}$ alkyl), heteroaryl($C_{1-6}$ alkyl), and heterocyclyl($C_{1-6}$ alkyl) are each substituted 1, 2, or 3 times, with a substituent selected from the group consisting of halogen and optionally substituted O—$C_{1-6}$-alkyl. In one aspect, the halogen is fluorine. In one embodiment, the ring system of one of the at least two of $R^4$, $R^5$, and $R^6$ independently selected from the group consisting of aryl($C_{1-6}$ alkyl), heteroaryl($C_{1-6}$ alkyl), heterocyclyl($C_{1-6}$ alkyl) is substituted 1 to 3 times, such as 1, 2, or 3 times with an optionally substituted O—$C_{1-6}$-alkyl, such as a fluorinated O—$C_{1-6}$-alkyl.

In yet another embodiment, at least two of $R^4$, $R^5$, and $R^6$ are optionally substituted aryl($C_{1-6}$ alkyl). In a preferred embodiment, at least two of $R^4$, $R^5$, and $R^6$ are optionally substituted benzyl.

As stated, at least two of $R^4$, $R^5$, and $R^6$ are independently selected from the group consisting of aryl($C_{1-6}$ alkyl), heteroaryl($C_{1-6}$ alkyl), heterocyclyl($C_{1-6}$ alkyl). Typically, the $C_{1-6}$ alkyl of said aryl($C_{1-6}$ alkyl), heteroaryl($C_{1-6}$ alkyl), heterocyclyl($C_{1-6}$ alkyl) is $C_{1-4}$ alkyl, such as methylene ($C_1$ alkyl), ethylene ($C_2$ alkyl), or propylene ($C_3$ alkyl), or butylene ($C_4$ alkyl), more typically a $C_1$ alkyl or $C_2$ alkyl, most typically a $C_1$ alkyl. In a suitable embodiment, the $C_{1-6}$ alkyl of said aryl($C_{1-6}$ alkyl), heteroaryl($C_{1-6}$ alkyl), heterocyclyl ($C_{1-6}$ alkyl) may be substituted so as to form a branched hydrocarbon.

In a combination of embodiments, at least two of $R^4$, $R^5$, and $R^6$ are an optionally substituted benzyl. One of $R^4$, $R^5$, and $R^6$ may be a 4-halo-benzyl group and one may be a 4-alkoxy-benzyl group. The 4-halo-benzyl group is typically a 4-fluoro-benzyl. The 4-alkoxy-benzyl group is typically a $C_{2-5}$ alkoxybenzyl or optionally fluorinated 4-methoxy-benzyl group such as a fluoromethoxy-benzyl, difluoromethoxy-benzyl, trifluoromethoxy-benzyl group, and 2,2,2-trifluoro-thoxy-benzyl.

As stated, the compounds of the invention may be selected from the group consisting of (i) 1-oxa-4,9-diaza-spiro[5.5]undecan-3-one; (ii) 1-oxa-3,8-diaza-spiro[4.5]decan-2-one; (iii) 1,3,8-triaza-spiro[4.5]decan-2-one; (iv) 1,2,9-triaza-spiro[5.5]undecan-3-one; (v) 1,2,8-triaza-spiro[4.5]decan-3-one; (vi) 1,2,8-triaza-spiro[4.5]decan-3-one (vii) 1,2,4,8-tetraaza-spiro[4.5]decan-3-one; (viii) 2,4,9-triaza-spiro[5.5]undecan-3-one; (ix) 2,8-diaza-spiro[4.5]decan-3-one (x) 2-oxa-4,9-diaza-spiro[5.5]undecan-3-one; (xi) 1-thia-3,8-diaza-spiro[4.5]decan-2-one; and (xii) 1-oxa-3,9-diaza-spiro [5.5]undecan-2-one.

Suitable embodiments of the compounds of the invention may be selected from the group consisting of 4-(4-Fluorobenzyl)-3-(4-methoxybenzyl)-8-methyl-1-oxa-3,8-diaza-spiro [4.5]decan-2-one; 3-(4-Ethoxybenzyl)-4-(4-fluorobenzyl)-8-methyl-1-oxa-3,8-diaza-spiro[4.5]decan-2-one; 4-(4-Fluorobenzyl)-8-methyl-3-(4-propoxybenzyl)-1-oxa-3,8-diaza-spiro[4.5]decan-2-one; 3-(4-Cyclopropylmethoxybenzyl)-4-(4-fluorobenzyl)-8-methyl-1-oxa-3,8-diaza-spiro[4.5]decan-2-one; 4-(4-Fluorobenzyl)-3-(4-isopropoxybenzyl)-8-methyl-1-oxa-3,8-diaza-spiro[4.5]decan-2-one; 3-(4-Butoxybenzyl)-4-(4-fluorobenzyl)-8-methyl-1-oxa-3,8-diaza-spiro[4.5]decan-2-one; 4-(4-Fluorobenzyl)-3-(4-isobutoxybenzyl)-8-methyl-1-oxa-3,8-diaza-spiro[4.5]decan-2-one; 3-(4-Difluoromethoxybenzyl)-4-(4-fluorobenzyl)-8-methyl-1-oxa-3,8-diaza-spiro[4.5]decan-2-one; 4-(4-Fluorobenzyl)-8-methyl-3-(4-trifluoromethoxybenzyl)-1-oxa-3,8-diaza-spiro[4.5]decan-2-one; 4-(4-Fluorobenzyl)-8-methyl-3-(4-pentoxybenzyl)-1-oxa-3,8-diaza-spiro[4.5]decan-2-one; 8-Ethyl-4-(4-fluorobenzyl)-3-(4-isobutoxybenzyl)-1-oxa-3,8-diaza-spiro[4.5]decan-2-one; 4-(4-Fluorobenzyl)-3-(4-isobutoxybenzyl)-8-isopropyl-1-oxa-3,8-diaza-spiro[4.5]decan-2-one; 8-Cyclopropylmethyl-4-(4-fluorobenzyl)-3-(4-isobutoxybenzyl)-1-oxa-3,8-diaza-spiro[4.5]decan-2-one; 8-Cyclohexylmethyl-4-(4-fluorobenzyl)-3-(4-isobutoxybenzyl)-1-oxa-3,8-diaza-spiro[4.5]decan-2-one; 8-Cyclopentyl-4-(4-fluorobenzyl)-3-(4-isobutoxybenzyl)-1-oxa-3,8-diaza-spiro[4.5]decan-2-one; 4-(4-Fluorobenzyl)-3-(4-isobutoxybenzyl)-8-(3-morpholin-4-yl-propyl)-1-oxa-3,8-diaza-spiro[4.5]decan-2-one; 8-(2-[1,3]Dioxolan-2-yl-ethyl)-4-(4-fluorobenzyl)-3-(4-isobutoxybenzyl)-1-oxa-3,8-diaza-spiro[4.5]decan-2-one; 4-(4-Fluorobenzyl)-3-(4- isobutoxybenzyl)-8-[2-(2-oxo-imidazolidin-1-yl)-ethyl]-1-oxa-3,8-diaza-spiro[4.5]decan-2-one; 4-(4-Fluorobenzyl)-3-(4-isobutoxybenzyl)-8-[3-(2-oxo-2,3-dihydro-benzoimidazol-1-yl)-propyl]-1-oxa-3,8-diaza-spiro[4.5]decan-2-one; 4-(4-Fluorobenzyl)-3-(4-isobutoxybenzyl)-8-(2-methyl-thiazol-4-yl-methyl)-1-oxa-3,8-diaza-spiro[4.5]decan-2-one; 4-(4-Chlorobenzyl)-3-(4-isobutoxybenzyl)-8-methyl-1-oxa-3,8-diaza-spiro[4.5]decan-2-one; 8-Ethyl-4-(4-chlorobenzyl)-3-(4-isobutoxybenzyl)-1-oxa-3,8-diaza-spiro[4.5]decan-2-one; 4-(4-Chlorobenzyl)-3-(4-isobutoxybenzyl)-8-isopropyl-1-oxa-3,8-diaza-spiro[4.5]decan-2-one; 8-Cyclopropylmethyl-4-(4-chlorobenzyl)-3-(4-isobutoxybenzyl)-1-oxa-3,8-diaza-spiro[4.5]decan-2-one; 8-Cyclohexylmethyl-4-(4-chlorobenzyl)-3-(4-isobutoxybenzyl)-1-oxa-3,8-diaza-spiro[4.5]decan-2-one; 8-(2-[1,3]Dioxolan-2-yl-ethyl)-4-(4-chlorobenzyl)-3-(4-isobutoxybenzyl)-1-oxa-3,8-diaza-spiro[4.5]decan-2-one; 4-(4-Chlorobenzyl)-3-(4-isobutoxybenzyl)-8-[2-(2-oxo-imidazolidin-1-yl)-ethyl]-1-oxa-3,8-diaza-spiro[4.5]decan-2-one; 3-(4-Difluoromethoxybenzyl)-4-(4-fluorobenzyl)-8-methyl-1-oxa-3,8-diaza-spiro[4.5]decan-2-one; 3-(4-Difluoromethoxybenzyl)-8-ethyl-4-(4-fluorobenzyl)-1-oxa-3,8-diaza-spiro[4.5]decan-2-one; 3-(4-Difluoromethoxybenzyl)-4-(4-fluorobenzyl)-8-isopropyl-1-oxa-3,8-diaza-spiro[4.5]decan-2-one; 8-Cyclopropylmethyl-3-(4-difluoromethoxybenzyl)-4-(4-fluorobenzyl)-1-oxa-3,8-diaza-spiro[4.5]decan-2-one; 8-Cyclohexylmethyl-3-(4-difluoromethoxybenzyl)-4-(4-fluorobenzyl)-1-oxa-3,8-diaza-spiro[4.5]decan-2-one; 3-(4-Difluoromethoxybenzyl)-8-(2-[1,3]dioxolan-2-yl-ethyl)-4-(4-fluorobenzyl)-1-oxa-3,8-diaza-spiro[4.5]decan-2-one; 3-(4-Difluoromethoxybenzyl)-4-(4-fluorobenzyl)-8-[2-(2-oxo-imidazolidin-1-yl)-ethyl]-1-oxa-3,8-diaza-spiro[4.5]decan-2-one; 8-Ethyl-4-(4-fluorobenzyl)-3-(4-trifluoromethoxybenzyl)-1-oxa-3,8-diaza-spiro[4.5]decan-2-one; 4-(4-Fluorobenzyl)-8-isopropyl-3-(4-trifluoromethoxybenzyl)-1-oxa-3,8-diaza-spiro[4.5]decan-2-one; 8-Cyclopropylmethyl-4-(4-fluorobenzyl)-3-(4-trifluoromethoxybenzyl)-1-oxa-3,8-diaza-spiro[4.5]decan-2-one; 8-Cyclohexylmethyl-4-(4-fluorobenzyl)-3-(4-trifluoromethoxybenzyl)-1-oxa-3,8-diaza-spiro[4.5]decan-2-one; 8-Cyclopentyl-4-(4-fluorobenzyl)-3-(4-trifluoromethoxybenzyl)-1-oxa-3,8-diaza-spiro[4.5]decan-2-one; 8-(2-[1,3]Dioxolan-2-yl-ethyl)-4-(4-fluorobenzyl)-3-(4-trifluoromethoxybenzyl)-1-oxa-3,8-diaza-spiro[4.5]decan-2-one; 4-(4-Fluorobenzyl)-8-[2-(2-oxo-imidazolidin-1-yl)-ethyl]-3-(4-trifluoromethoxybenzyl)-1-oxa-3,8-diaza-spiro[4.5]decan-2-one; 8-Ethyl-4-(4-fluorobenzyl)-3-(4-propoxybenzyl)-1-oxa-3,8-diaza-spiro[4.5]decan-2-one; 4-(4-Fluorobenzyl)-8-isopropyl-3-(4-propoxybenzyl)-1-oxa-3,8-diaza-spiro[4.5]decan-2-one; 8-Cyclopropylmethyl-4-(4-fluorobenzyl)-3-(4-propoxybenzyl)-1-oxa-3,8-diaza-spiro[4.5]decan-2-one; 8-Cyclohexylmethyl-4-(4-fluorobenzyl)-3-(4-propoxybenzyl)-1-oxa-3,8-diaza-spiro[4.5]decan-2-one; 8-Cyclopentyl-4-(4-fluorobenzyl)-3-(4-propoxybenzyl)-1-oxa-3,8-diaza-spiro[4.5]decan-2-one; 8-(2-[1,3]Dioxolan-2-yl-ethyl)-4-(4-fluorobenzyl)-3-(4-propoxybenzyl)-1-oxa-3,8-diaza-spiro[4.5]decan-2-one; 4-(4-Fluorobenzyl)-8-[2-(2-oxo-imidazolidin-1-yl)-ethyl]-3-(4-propoxybenzyl)-1-oxa-3,8-diaza-spiro[4.5]decan-2-one; 3-(4-Cyclopropylmethoxybenzyl)-8-ethyl-4-(4-fluorobenzyl)-1-oxa-3,8-diaza-spiro[4.5]decan-2-one; 3-(4-Cyclopropylmethoxybenzyl)-4-(4-fluorobenzyl)-8-isopropyl-1-oxa-3,8-diaza-spiro[4.5]decan-2-one; 3-(4-Cyclopropylmethoxybenzyl)-8-cyclopropylmethyl-4-(4-fluorobenzyl)-1-oxa-3,8-diaza-spiro[4.5]decan-2-one; 3-(4-Cyclopropylmethoxybenzyl)-8-(2-[1,3]dioxolan-2-yl-ethyl)-4-(4-fluorobenzyl)-1-oxa-3,8-diaza-spiro[4.5]decan-2-one; 3-(4-Cyclopropylmethoxybenzyl)-4-(4-fluorobenzyl)-8-[2-(2-oxo-imidazolidin-1-yl)-ethyl]-1-oxa-3,8-diaza-spiro[4.5]decan-2-one; 8-(2-[1,3]-Dioxan-2-yl-ethyl)-4-(4-fluorobenzyl)-3-(4-isobutoxybenzyl)-1-oxa-3,8-diaza-spiro[4.5]decane-2-one; 4-(4-Fluorobenzyl)-3-(4-isobutoxybenzyl)-8-{3-[(S)-4-isopropyl-2-oxo-oxazolidin-3-yl]-propyl}-1-oxa-3,8-diaza-spiro[4.5]decane-2-one; 1-(4-Fluorobenzyl)-2-(4-methoxybenzyl)-8-methyl-1,2,8-triaza-spiro[4.5]decan-3-one; 2-(4-Ethoxybenzyl)-1-(4-fluorobenzyl)-8-methyl-1,2,8-triaza-spiro[4.5]decan-3-one; 1-(4-Fluorobenzyl)-8-methyl-2-(4-propoxybenzyl)-1,2,8-triaza-spiro[4.5]decan-3-one; 1-(4-Fluorobenzyl)-2-(4-isopropoxybenzyl)-8-methyl-1,2,8-triaza-spiro[4.5]decan-3-one; 2-(4-Butoxybenzyl)-1-(4-fluorobenzyl)-8-methyl-1,2,8-triaza-spiro[4.5]decan-3-one; 2-(4-Cyclopropylmethoxybenzyl)-1-(4-fluorobenzyl)-8-methyl-1,2,8-triaza-spiro[4.5]decan-3-one; 1-(4-Fluorobenzyl)-2-(4-isobutoxybenzyl)-8-methyl-1,2,8-triaza-spiro[4.5]decan-3-one; 2-(4-Difluoromethoxybenzyl)-1-(4-fluorobenzyl)-8-methyl-1,2,8-triaza-spiro[4.5]decan-3-one; 1-(4-Fluorobenzyl)-8-methyl-2-(4-trifluoromethoxybenzyl)-1,2,8-triaza-spiro[4.5]decan-3-one; 1-(4-Fluorobenzyl)-8-methyl-2-(4-pentoxybenzyl)-1,2,8-triaza-spiro[4.5]decan-3-one; 1-(4-Chlorobenzyl)-2-(4-ethoxybenzyl)-8-methyl-1,2,8-triaza-spiro[4.5]decan-3-one; 1-(4-Chlorobenzyl)-8-methyl-2-(4-propoxybenzyl)-1,2,8-triaza-spiro[4.5]decan-3-one; 1-(4-Chlorobenzyl)-2-(4-isobutoxybenzyl)-8-methyl-1,2,8-triaza-spiro[4.5]decan-3-one; 1-(4-Chlorobenzyl)-2-(4-cyclopropylmethoxybenzyl)-8-methyl-1,2,8-triaza-spiro[4.5]decan-3-one; 1-(4-Chlorobenzyl)-2-(4-difluoromethoxybenzyl)-8-methyl-1,2,8-triaza-spiro[4.5]decan-3-one; 1-(4-Ethylbenzyl)-2-(4-ethoxybenzyl)-8-methyl-1,2,8-triaza-spiro[4.5]decan-3-one; 1-(4-Ethylbenzyl)-2-(4-isopropoxybenzyl)-8-methyl-1,2,8-triaza-spiro[4.5]decan-3-one; 1-(4-Ethylbenzyl)-2-(4-isobutoxybenzyl)-8-methyl-1,2,8-triaza-spiro[4.5]decan-3-one; 1-(4-Ethylbenzyl)-2-(4-cyclopropylmethoxybenzyl)-8-methyl-1,2,8-triaza-spiro[4.5]decan-3-one; 1-(4-Ethylbenzyl)-8-methyl-2-(4-trifluoromethoxybenzyl)-1,2,8-triaza-spiro[4.5]decan-3-one; 2-(4-Difluoromethoxybenzyl)-1-(4-fluorobenzyl)-8-ethyl-1,2,8-triaza-spiro[4.5]decan-3-one; 2-(4-Difluoromethoxybenzyl)-1-(4-fluorobenzyl)-8-isopropyl-1,2,8-triaza-spiro[4.5]decan-3-one; 2-(4-Difluoromethoxybenzyl)-1-(4-fluorobenzyl)-8-cyclopropylmethyl-1,2,8-triaza-spiro[4.5]decan-3-one; 2-(4-Difluoromethoxybenzyl)-1-(4-fluorobenzyl)-8-(2-[1,3]dioxolan-2-yl-ethyl)-1,2,8-triaza-spiro[4.5]decan-3-one; 8-Ethyl-1-(4-fluorobenzyl)-2-(4-isobutoxybenzyl)-1,2,8-triaza-spiro[4.5]decan-3-one; 1-(4-Fluorobenzyl)-2-(4-isobutoxybenzyl)-8-isopropyl-1,2,8-triaza-spiro[4.5]decan-3-one; 8-Cyclopropylmethyl-1-(4-fluorobenzyl)-2-(4-isobutoxybenzyl)-1,2,8-triaza-spiro[4.5]decan-3-one; 8-(2-[1,3]dioxolan-2-yl-ethyl)-1-(4-fluorobenzyl)-2-(4-isobutoxybenzyl)-1,2,8-triaza-spiro[4.5]decan-3-one; 4-(4-Ethoxybenzyl)-5-(4-fluorobenzyl)-9-methyl-1-oxa-4,9-diaza-spiro[5.5]undecan-3-one; 5-(4-Fluorobenzyl)-9-methyl-4-(4-propoxybenzyl)-1-oxa-4,9-diaza-spiro[5.5]undecan-3-one; 5-(4-fluorobenzyl)-4-(4-isobutoxybenzyl)-9-methyl-1-oxa-4,9-diaza-spiro[5.5]undecan-3-one; 5-(4-fluorobenzyl)-9-methyl-4-(4-trifluoromethoxybenzyl)-1-oxa-4,9-diaza-spiro[5.5]undecan-3-one; 5-(4-Chlorobenzyl)-4-(4-isobutoxybenzyl)-9-methyl-1-oxa-4,9-diaza-spiro[5.5]undecan-3-one; 5-(4-Chlorobenzyl)-4-(4-cyclopropylmethoxybenzyl)-9-methyl-1-oxa-4,9-diaza-spiro[5.5]undecan-3-one; 9-Ethyl-5-(4-fluorobenzyl)-4-(4- propoxybenzyl)-1-oxa-4,9-diaza-spiro[5.5]undecan-3-one; 1-(4-Fluorobenzyl)-2-(4-ethoxybenzyl)-9-methyl-1,2,9-triaza-spiro[5.5]undecan-3-one; 1-(4-Fluorobenzyl)-2-(4-cyclopropylmethoxybenzyl)-9-methyl-1,2,9-triaza-spiro[5.5]undecan-3-one; 1-(4-Fluorobenzyl)-2-(4-isobutoxybenzyl)-9-methyl-1,2,9-triaza-spiro[5.5]undecan-3-one; 1-(4-Fluorobenzyl)-2-(4-propoxybenzyl)-9-methyl-1,2,9-triaza-spiro[5.5]undecan-3-one; 1-(4-Ethylbenzyl)-2-(4-isobutoxybenzyl)-9-methyl-1,2,9-triaza-spiro[5.5]undecan-3-one; 1-(4-Fluorobenzyl)-2-(4-cyclopropylmethoxybenzyl)-9-ethyl-1,2,9-triaza-spiro[5.5]undecan-3-one; 2-(4-Ethoxybenzyl)-1-(4-fluorobenzyl)-8-methyl-1,2,4,8-tetraaza-spiro[4.5]decan-3-one; 1-(4-Fluorobenzyl)-2-(4-isobutoxybenzyl)-8-methyl-1,2,4,8-tetraaza-spiro[4.5]decan-3-one; 2-(4-Difluoromethoxybenzyl)-1-(4-fluorobenzyl)-8-methyl-2,8-diaza-spiro[4.5]decan-3-one; 1-(4-Fluorobenzyl)-2-(4-isobutoxybenzyl)-8-methyl-2,8-diaza-spiro[4.5]decan-3-one; 2-(4-Cyclopropylmethoxybenzyl)-1-(4-fluorobenzyl)-8-methyl-2,8-diaza-spiro[4.5]decan-3-one; 8-Ethyl-1-(4-fluorobenzyl)-2-(4-isobutoxybenzyl)-2,8-diaza-spiro[4.5]decan-3-one; 8-(2-[1,3]Dioxolan-2-yl-ethyl)-1-(4-fluorobenzyl)-2-(4-isobutoxybenzyl)-2,8-diaza-spiro[4.5]decan-3-one; 3-(4-Difluoromethoxybenzyl)-4-(4-fluorobenzyl)-8-methyl-1,3,8-triaza-spiro[4.5]decan-2-one; 4-(4-Fluorobenzyl)-3-(4-isobutoxybenzyl)-8-methyl-1,3,8-triaza-spiro[4.5]decan-2-one; 3-(4-Cyclopropylmethoxybenzyl)-4-(4-fluorobenzyl)-8-methyl-1,3,8-triaza-spiro[4.5]decan-2-one; 8-Ethyl-4-(4-fluorobenzyl)-3-(4-isobutoxybenzyl)-1,3,8-triaza-spiro[4.5]decan-2-one; 8-(2-[1,3]Dioxolan-2-yl-ethyl)-4-(4-fluorobenzyl)-3-(4-isobutoxybenzyl)-1,3,8-triaza-spiro[4.5]decan-2-one; 1-(4-Fluorobenzyl)-2-(4-ethoxybenzyl)-9-methyl-2,4,9-triaza-spiro[5.5]undecan-3-one; 1-(4-Fluorobenzyl)-2-(4-cyclopropylmethoxybenzyl)-9-methyl-2,4,9-triaza-spiro[5.5]undecan-3-one; 1-(4-Fluorobenzyl)-2-(4-isobutoxybenzyl)-9-methyl-2,4,9-triaza-spiro[5.5]undecan-3-one; 1-(4-Fluorobenzyl)-2-(4-trifluoromethoxybenzyl)-9-methyl-2,4,9-triaza-spiro[5.5]undecan-3-one; 1-(4-Fluorobenzyl)-2-(4-isobutoxybenzyl)-9-ethyl-2,4,9-triaza-spiro[5.5]undecan-3-one; 4-(4-Ethoxybenzyl)-5-(4-fluorobenzyl)-9-methyl-1-oxa-3,9-diaza-spiro[5.5]undecan-2-one; 3-(4-Ethoxybenzyl)-5-(4-fluorobenzyl)-9-methyl-1-oxa-3,9-diaza-spiro[5.5]undecan-2-one; 3-(4-Ethoxybenzyl)-4-(4-fluorobenzyl)-9-methyl-1-oxa-3,9-diaza-spiro[5.5]undecan-2-one; 5-(4-Fluorobenzyl)-4-(4-propoxybenzyl)-9-methyl-1-oxa-3,9-diaza-spiro[5.5]undecan-2-one; 5-(4-Fluorobenzyl)-3-(4-propoxybenzyl)-9-methyl-1-oxa-3,9-diaza-spiro[5.5]undecan-2-one; 4-(4-Fluorobenzyl)-3-(4-propoxybenzyl)-9-methyl-1-oxa-3,9-diaza-spiro[5.5]undecan-2-one; 5-(4-Fluorobenzyl)-4-(4-isobutoxybenzyl)-9-methyl-1-oxa-3,9-diaza-spiro[5.5]undecan-2-one; 4-(4-Fluorobenzyl)-3-(4-isobutoxybenzyl)-9-methyl-1-oxa-3,9-diaza-spiro[5.5]undecan-2-one; 4-(4-Ethoxybenzyl)-5-(4-fluorobenzyl)-9-methyl-2-oxa-4,9-diaza-spiro[5.5]undecan-3-one; 5-(4-Fluorobenzyl)-4-(4-methoxybenzyl)-9-methyl-2-oxa-4,9-diaza-spiro[5.5]undecan-3-one; 5-(4-Fluorobenzyl)-4-(4-propoxybenzyl)-9-methyl-2-oxa-4,9-diaza-spiro[5.5]undecan-3-one; 5-(4-Fluorobenzyl)-4-(4-isobutoxybenzyl)-9-methyl-2-oxa-4,9-diaza-spiro[5.5]undecan-3-one; 4-(4-Ethoxybenzyl)-5-(4-fluorobenzyl)-9-methyl-2-oxa-4,9-diaza-spiro[5.5]undecan-3-one; 3-(4-Ethoxybenzyl)-4-(4-fluorobenzyl)-8-methyl-1-thia-3,8-diaza-spiro[4.5]decan-2-one; 4-(4-Fluorobenzyl)-3-(4-methoxybenzyl)-8-methyl-1-thia-3,8-diaza-spiro[4.5]decan-2-one; 4-(4-Fluorobenzyl)-3-(4-propoxybenzyl)-8-methyl-1-thia-3,8-diaza-spiro[4.5]decan-2-one; 4-(4-Fluorobenzyl)-3-(4-isobutoxybenzyl)-8-methyl-1-thia-3,8-diaza-spiro[4.5]decan-2-one.

Certain embodiments of the compounds of the invention possess chirality or have a chiral centre. The invention provides compounds of the invention in their racemic form, enantio-enriched forms or enantiopure forms. The present investigators have isolated individual enantiomers of high enantiomeric excess of certain chiral embodiments of the compounds of the invention and found non-identical activity of the two forms towards monoamine receptors.

A preferred embodiment of compounds of the invention is comprised of compounds of formula I which are homochiral to the compound of Formula II.

The Examples demonstrate suitable methods of preparation of many of the compounds of the invention, said methods being adaptable to the preparation of all of the compounds of the invention by methods known to the person skilled in the art. Pharmaceutically acceptable salts of the compounds of the formula I are also within the scope of the invention.

The compounds of the invention may in general be prepared by routes such as those summarised below. Many of the synthetic routes described below require protecting group strategies, which include groups such as those described in T. W. Greene and P. G. M. Wuts, *Protective Groups in Organic Chemistry*, 3. Ed. John Wiley & Sons, 1999, and they should be chosen in such a way, that they are stable to the reaction conditions applied and readily removed at a convenient stage using methodology known from the art. Typical protecting groups are N-Boc, N-Cbz, N-Bn.

Cyclisation of the appropriate intermediates may be generally achieved with phosgene or its analogues such as CDI, with chloroacetylchloride or equivalents thereof or by treatment with carbondisulfide and subsequent oxidation.

Introduction of the desired piperidine substituent ($R^1$) can generally be achieved, after N-deprotection if required, by alkylation or by reductive amination.

Compounds of the invention in which m=1, Z=CH and X=O or $OCH_2$ may be synthesized from suitably protected 4-piperidone as described by Bassus et al. (*Eur. J. Med. Chem.-Chim. Ther.* 9:416-423 (1974)). Alkylation of the carbamate nitrogen and introduction of the desired piperidine N-substituent leads to the 3,5-disubstituted spirocycle. 3,4 or 4,5-disubstituted derivatives may be prepared as described by Fisera et al. (*Monatsh. Chem.* 125:909-919 (1994)), via an appropriately substituted isoxazoline, followed by reductive cleavage. Cyclisation of the resulting γ-aminoalcohols gives the desired spirocycles. Alternatively, 4,5-disubstituted or 3,4,5-trisubstituted spirocycles may be prepared from an appropriate β-ketoester by reaction with a halide to introduce the 5-substituent, reductive amination (with a primary amine for the 3-substituent), treatment with allyl magnesium bromide, cyclisation as described above, oxidative cleavage of the double bonds (e.g. by ozonolysis) and formation of the piperidine ring by reductive amination.

Compounds of the invention in which m=1, Z=N and X=O or $OCH_2$ may be prepared by a Strecker synthesis involving an appropriate aldehyde and e.g. tert-butyl carbazate. The nitrile may be transformed into an ester, which is reacted with allyl magnesium bromide, followed by oxidative cleavage of the two olefins, formation of the piperidine by reductive amination. Alkylation, deprotection of the hydrazide and cyclisation gives the desired spirocycles. Depending on the desired substituents and their positions, these steps may be inversed and additional protection steps of functional groups may be required. Alternatively, the compounds may be obtained from an appropriate β-ketoester by reaction with a bis(2-chloroethyl) amine derivative to form the piperidine ring. Reductive amination, saponification and Curtius rearrangement lead to the cyclic urea derivative.

Compounds of the invention in which m=1, Z=N and X=N(R) may be prepared adapting methods described by Bhatia et al. (*J. Med. Chem.* 39:3938-3950 (1996)) starting from the suitably protected Strecker-product 4-amino-4-cyano-piperidine.

Compounds of the invention in which m=0, Z=CH and X=$CH_2CH_2$ may be synthesized by Michael addition of a nitrile-derivative to suitably protected 4-methoxycarbonyl-methylenepiperidine, reduction of the nitrile-group to the amine, followed by lactam ring formation, alkylation of the resulting amide and introduction of the desired piperidine substituent.

Compounds of the invention in which m=0, Z=CH and X=$CH_2O$ may be prepared from the appropriate β-ketoester by reaction with a suitably protected bis(2-chloroethyl) amine. Reductive amination, followed by reduction of the nitrile to the alcohol followed by cyclisation and introduction of the piperidine substituent by alkylation or reductive amination leads to the desired spirocycle.

Compounds of the invention in which m=0, Z=CH and X=$CH_2N$ may be prepared from the appropriate β-ketonitrile by reaction with a suitably protected bis(2-chloroethyl) amine. Reductive amination, followed by reduction of the nitrile to the amine followed by cyclisation and introduction of the piperidine substituent by alkylation or reductive amination leads to the desired spirocycle.

Compounds of the invention in which m=0, Z=CH and X=$OCH_2$ may be prepared as described in Example 1.

Compounds of the invention in which m=0, Z=N and X=$CH_2CH_2$ may be prepared from protected 8-aza-1-oxa-spiro[4.5]decan-2-one (Mullen et al. *J. Med. Chem.* 43:4045 (2000)) by reaction with hydrazine, then S-ethyltrifluorothioacetate, followed by a Mitsunobu reaction according to Meng et al. (*Tetrahedron* 47:6251 (1991)). The appropriate substituents in 1,2- and 9-positions are introduced by alkylation and/or reductive amination.

Compounds of the invention in which m=0, Z=N and X=$CH_2O$ may be prepared by a Strecker synthesis from suitably protected 4-piperidone and a carbazate (or an appropriate hydrazine). Transformation of the resulting nitrile into the alcohol, cyclisation using methods described above, alkylation (after basic hydrolysis of the exocyclic carbazate function if present) and introduction of the piperidine N-substituent leads to the desired compound.

Compounds of the invention in which m=0, Z=N and X=$CH_2N$ may be prepared using the same strategy as for the preparation of 1,2,9-triaza-4-oxa-spiro[5.5]undecan-3-one, except that the nitrile is reduced to the corresponding amine.

Compounds of the invention in which m=0, Z=CH and X=$CH_2$ may be synthesized by Michael addition of a nitro-derivative to suitably protected 4-methoxycarbonyl-methylenepiperidine, reduction of the nitro-group to the amine, followed by lactam ring formation, alkylation of the resulting amide and introduction of the desired piperidine substituent.

Compounds of the invention in which m=0, Z=CH and X=O may be prepared as described in Example 1. Alternatively, a nitroaldol reaction may be used to obtain the desired intermediate 1,2-aminoalcohol after reduction of the nitro-group, followed by cyclisation. Alternatively, the compounds may be prepared by epoxidation of an appropriate olefin, obtained by Wittig or Horner-Wadsworth-Emmons reactions from suitably protected 4-piperidone. Epoxide opening with ammonia or a primary amine, followed by cyclisation with a phosgene equivalent, alkylation of the carbamates if required and introduction of the desired piperidine substituent by alkylation or reductive amination leads to the target compound. Besides the preparation of enantiopure compound as described in Example 1, an enantioselective modification may include an asymmetric epoxidation method of the olefin as described in the literature, e.g. Jacobsen or others. Alternatively, Sharpless asymmetric dihydroxylation method may be used followed by epoxide ring formation. Alternatively, suitably protected 4-methoxycarbonyl-methylenepiperidine may be reduced to the allyl alcohol which is subjected to Sharpless asymmetric epoxidation according to literature procedure. Epoxide opening with a metallorganic reagent and oxidation of the resulting primary alcohol leads to the β-hydroxy carboxylic acid, which is converted into the desired spirocyclic enantiomer as described in Example 1. Alternatively, suitably protected 4-methoxycarbonyl-methylenepiperidine may be converted to an enantiomerically pure epoxide by Jacobsen epoxidation, followed by ring opening with ammonia or an appropriate amine, reaction with a metallorganic reagent with the ester group, reduction, cyclisation, alkylation if required and introduction of the piperidine substituent. Alternatively, the stereocenter may be introduced by using an appropriate α-amino acid ester as the chiral template. Reaction with allyl magnesium bromide, cyclisation, oxidative cleavage of the allyl groups, formation of the piperidine ring by reductive amination and final alkylation of the carbamate leads to the desired enantiomerically pure derivative.

Compounds of the invention in which m=0, Z=CH and X=N or $NCH_2$ may be prepared by a Strecker synthesis involving suitably protected 4-piperidone and an appropriate primary amine. Reaction of the resulting nitrile with a Grignard reagent gives the ketone, which is then subjected to a reductive amination. Cyclisation of the resulting diamine (after deprotection step if necessary), with phosgene or an equivalent thereof leads to the cyclic urea. Alkylation or reductive amination steps may be used to introduce N-piperidine substituents. In a similar way, the 6-membered analogue (X=$NCH_2$) may be obtained by using chloroacetyl chloride or a similar reagent for cyclisation (additional use of protecting groups may be necessary).

Compounds of the invention in which m=0, Z N and X=$CH_2$ may be prepared as outlined in Example 1.

Compounds of the invention in which m=0, Z=N and X=N(R) may be obtained according to literature methods (Gstach et al. *Synthesis* 803-808 (1990)) by treatment of a suitably protected 4-piperidone by reaction with a hydrazine derivative and reaction of the intermediate hydrazone with potassium cyanate. Alkylation and/or reductive amination after deprotection may be used to introduce the desired substituents.

Alternatively, compounds of the invention in which X=S or $SCH_2$ or $CH_2S$ may be obtained as described by routes described for the equivalent compounds bearing X=O, $OCH_2$ or $CH_2O$ by transforming, prior to cyclisation, the appropriate hydroxyl group into a thiol using well known literature procedures (e.g. treatment with acetyl chloride and substitution with benzylthiol and conversion to the free mercaptane). Similarly, the hydroxyl group may be converted into the corresponding amines, which constitutes an alternative way to access some compounds of the invention in which X=N(R), $N(R)CH_2$, $CH_2(R)$.

Compounds of the invention in which Y=S may be prepared from the corresponding compounds in which Y=O by treatment with e.g. the Lawesson reagent or bis(tricyclohexyltin)sulfide and $BCl_3$ or other sulphur-transferring reagents.

The invention also provides pharmaceutical compositions including invention compounds. In one embodiment, a composition includes a compound of formula I, a pharmaceutically acceptable salt thereof or a stereoisomer, together with a pharmaceutically acceptable carrier or excipient.

In some embodiments, the compounds of the invention are effective in inhibiting the activity of a monoamine receptor. The invention therefore provides methods of inhibiting an activity of a monoamine receptor. In one embodiment, a method includes contacting the monoamine receptor or a system containing the monoamine receptor with an effective amount of one or more of the compounds of the invention to inhibit activity of the monoamine receptor. The invention also provides methods of inhibiting activation of a monoamine receptor. In one embodiment, a method includes contacting a monoamine receptor or a system containing a monoamine receptor with an effective amount of one or more of the compounds of the invention to inhibit activation of the monoamine receptor.

Typically, the monoamine receptor is a serotonin receptor. Typically, the serotonin receptor is the 5-HT2A subclass. The serotonin receptor may be selected from the central nervous system or the peripheral nervous system. In various aspects, the serotonin receptor is found in the central nervous system or in blood cells or platelets. In further aspects, the serotonin receptor is mutated or modified.

Typically, the activity inhibited by the method of the invention is signaling activity. Moreover, the activity or activation is typically constitutive. The activity is typically associated with serotonin receptor activation.

Also provided are methods of inhibiting activation of a monoamine receptor. In one embodiment, a method includes contacting the monoamine receptor or a system containing the monoamine receptor with an effective amount of one or more of the compounds of the invention to inhibit activation of the monoamine receptor. In one aspect, the activation inhibited is an activation related to the action of an agonistic agent. The agonistic agent may exogenous or endogenous.

Further provided are methods of treating a disease condition associated with at least one monoamine receptor. In one embodiment, a method includes administering to a subject in need of such treatment a therapeutically effective amount of one or more of the compounds of the invention to treat the disease condition associated with at least one monoamine receptor.

As disclosed herein, the disease condition may be associated with dysfunction of at least one monoamine receptor. Alternatively or additionally, the disease condition may be associated with activation of a monoamine receptor. The disease condition may be furthermore associated with increased activity of monoamine receptor. The disease conditions may be selected from the group consisting of schizophrenia, psychosis, drug-induced psychosis, treatment-induced psychosis, migraine, hypertension, thrombosis, vasospasm, ischemia, depression, anxiety, sleep disorders and appetite disorders.

The invention also provides uses of a compound of formula I for the preparation of a medicament for the treatment of a disease condition associated with a monoamine receptor. In particular embodiments, uses of a compound of formula I for the preparation of a medicament for the treatment of a disease is selected from the group consisting of schizophrenia, psychosis (including drug- or treatment-induced psychosis such as hallucinosis induced by medications used in the treatment of Parkinson's disease), migraine, hypertension, thrombosis, vasospasm, ischemia, depression, anxiety (including general anxiety disorder), sleep disorders and appetite disorders.

A particular aspect of the invention is a method of treating and use of a compound of formula I for the preparation of a medicament for treating schizophrenia. In one embodiment, a method includes administering to a subject in need of such treatment a therapeutically effective amount of one or more of the compounds of the invention to treat schizophrenia. In another embodiment, the use of a compound of formula I is for the preparation of a medicament for the treatment of schizophrenia.

A particular aspect of the invention is a method of treating and use of a compound of formula I for the preparation of a medicament for treating migraine. In one embodiment, a method includes administering to a subject in need of such treatment a therapeutically effective amount of one or more of the compounds of the invention to treat migraine. In another embodiment, the use of a compound of formula I is for the preparation of a medicament for the treatment of migraine.

Another particular aspect of the invention is a method of treating and use of a compound of formula I for the preparation of a medicament for treating drug-induced or treatment-induced psychosis or hallucinosis. In one embodiment, a method includes administering to a subject in need of such treatment a therapeutically effective amount of one or more of the compounds of the invention to treat drug- or treatment-induced hallucinosis or psychosis. In another embodiment, the use of a compound of formula I is for the preparation of a medicament for the treatment of drug- or treatment-induced hallucinosis or psychosis.

Given the nature of the activity of the serotonin receptor, its modulation may have more than one downstream effect and be beneficial in the treatment of more than one disease state. Certain compounds of the invention may be best suited for the treatment of schizophrenia whereas other compounds of the invention may be best suited for the treatment of for instance migraine, hypertension, thrombosis, vasospasm, ischemia, depression, anxiety, sleep disorders and appetite disorders. Thus, in additional aspects, the invention provides methods of treating psychosis, migraine, hypertension, thrombosis, vasospasm, ischemia, depression, anxiety, sleep disorders and appetite disorders. In various embodiments, a method includes administering to a subject in need of such treatment a therapeutically effective amount of one or more of the compounds of the invention to treat psychosis, migraine, hypertension, thrombosis, vasospasm, ischemia, depression, anxiety, sleep disorder or an appetite disorder. Also provided are uses of a compound of formula I for the preparation of a medicament for the treatment of psychosis, migraine, hypertension, thrombosis, vasospasm, ischemia, depression, anxiety, sleep disorders and appetite disorders.

Further provided are methods for identifying a genetic polymorphism predisposing a subject to being responsive to one or more of the compounds of formula I. In one embodiment, a method includes:

administering to a subject a therapeutically effective amount of the compound;

measuring the response of said subject to said compound, thereby identifying a responsive subject having an ameliorated disease condition associated with a monoamine receptor; and identifying a genetic polymorphism in the responsive subject, wherein the genetic polymorphism predisposes a subject to being responsive to the compound. Typically, the ameliorated disease condition is associated with the 5-HT class or 5-HT2A subclass of monoaminergic receptors.

The invention additionally provides methods for identifying a subject suitable for treatment with one or more of the compounds of formula I. In one embodiment, a method includes detecting the presence of a polymorphism in a subject wherein the polymorphism predisposes the subject to being responsive to the compound, and wherein the presence of the polymorphism indicates that the subject is suitable for treatment with one or more of the compounds of formula I.

The Examples demonstrate suitable preparation methods of non-limiting embodiments of the invention and demonstrate the selectivity and activity of the compounds of the invention at monoamine receptors.

EXAMPLES

Example 1

Synthetic Chemistry

General methods. $^1$H NMR spectra were recorded at 400 MHz, whereas $^{13}$C NMR spectra were measured at 100 MHz with proton decoupling at ambient temperature. Chemical shifts are given in δ-values [ppm] referenced to the residual solvent peak chloroform (CDCl$_3$) at 7.26 and 77.0 ppm and methanol (CD$_3$OD) at 3.31 and 49.2 ppm. Coupling constants, J, are reported in Hertz.

Materials and solvents were of the highest grade available from commercial sources and used without further purification. Acidic ion-exchange solid phase extraction cartridges were MEGA BE-SCX from Varian.

General LC-MS procedure. HPLC/MS analyses were performed using either of two general methods (Method A or Method B).

Method A: Agilent HP1100 HPLC/MSD. G1312A binary pump, G1313A autosampler, G1316A column compartment, G1315A diode array detector (190-450 nm), 1946A MSD, electrospray ionization.

Chromatography: mobile phase: 8 mM ammoniumacetate in water/acetonitrile. Gradient start at 70% org. up to 100% org. over 12 min, down to 70% org. over 0.5 min, held for 3.5 min. Total runtime 16 min. Flowrate 1 mL/min Column: Phenomenex Luna C$_{18}$(2) 3 µm, 75×4.6 mm.

MS parameters. Drying gas, 10 L/min. Nebulizer pressure, 40 psig. Gas temp, 350° C. VCap, 4000.

Method B: Waters/Micromass HPLC/MS. 600 LC-pump, 2700 sample manager, 996 diode array detector (190-450 nm), Micromass ZMD-mass-spectrometer, electrospray ionization.

Chromatography: mobile phase: 10 mM ammoniumacetate in water/acetonitrile. Gradient start at 30% org. for 0.5 min, up to 100% org. over 9.5 min, held for 2 min, down to 30% org. over 0.5 min, held for 5.5 min. Total run time 18 min. Flowrate, 1 mL/min.

Column: Phenomenex Luna C$_{18}$(2) 3 µm, 75×4.6 mm.

MS parameters. Desolvation gas, 404 L/h. Capillary, 5.3 kV. Cone, 36 V. Extractor, 3 V. Source block temp, 130° C. Desolvation temp, 250° C.

4-(4-Fluorobenzyl)-3-(4-isobutoxybenzyl)-8-methyl-1-oxa-3,8-diaza-spiro[4.5]decan-2-one, hydrochloride (69NLS75)

Preparation of 4-[1-Carboxy-2-(4-fluorophenyl)-ethyl]-4-hydroxy-1-methyl-piperidine-(69NLS42)

n-Butyllithium (1.6 M in hexane, 18.8 mL, 30 mmol) was added dropwise under stirring over 5 min to a cooled solution of N,N-diisopropylamine (4.2 mL, 30 mmol) in THF (25 mL) at −40° C. The solution was warmed to 0° C. and a solution of 3-(4-fluoro-phenyl)propionic acid (2.53 g, 15 mmol) in THF (20 mL) was added. The mixture was stirred for 30 min at rt, cooled to −78° C. and N-methylpiperidone (2.2 mL, 18 mmol) added dropwise over 15 min. The solution was allowed to warm to rt and poured into a stirred mixture of diethylether (100 mL) and water (60 mL). The organic layer was discarded, the aqueous layer extracted with another portion of diethylether. The aqueous layer was acidified with 4 M aq. HCl and extracted once with dichloromethane and with n-butanol (3×100 mL). The combined n-butanol-extracts were concentrated in vacuo, giving 69NLS42 as a light-yellow oil, which is used without further purification.

$R_f$=0.13 (MeOH/CH$_2$Cl$_2$ 1:9).

Preparation of 4-(4-Fluorobenzyl)-8-methyl-1-oxa-3,8-diaza-spiro[4.5]decan-2-one (69NLS44)

The crude piperidine derivative 69NLS42 (ca. 15 mmol) was dissolved in toluene (200 mL), triethylamine (4.18 mL, 30 mmol) and diphenylphosphoryl azide (3.88 mL, 18 mmol) were added, and the mixture refluxed overnight. The solvent was removed in vacuo, the residue dissolved in dichloromethane (200 mL) and extracted with 1M HCl (3×100 mL). The combined aqueous extracts were basified with 20% aq. KOH solution and extracted with dichloromethane (3×150 mL). The combined organic layers were dried over Na$_2$SO$_4$, filtered and evaporated to give 69NLS44 (2.06 g, 49% over two steps) as a yellow solid, which was used without further purification.

$R_f$=0.25 (MeOH/CH$_2$Cl$_2$ 1:9). LCMS m/z 278 [M+H]$^+$. HPLC $t_R$=1.9 min (method B).

Preparation of 4-isobutoxy benzyl bromide (69NLS69)

The alkylating agent was obtained according to literature procedures from p-cresol by Williamson ether synthesis, followed by a Wohl-Ziegler bromination.

4-(4-Fluorobenzyl)-3-(4-isobutoxybenzyl)-8-methyl-1-oxa-3,8-diaza-spiro[4.5]decan-2-one, hydrochloride (69NLS75)

The oxazolidinone 69NLS44 (crude, ca. 7 mmol) was dissolved in DMF/THF (1:9, 50 mL), sodium hydride (50% in oil, 0.67 g, 14 mmol) added and the suspension stirred at rt for 30 min, before the dropwise addition of the bromide 69NLS69 (1.5 g, 7 mmol). The mixture was stirred at rt for 4 h and then partitioned between ethyl acetate and water. The organic layer was separated and the aqueous layer extracted twice with ethyl acetate. The combined organic extracts were dried over Na$_2$SO$_4$, filtered and concentrated in vacuo. The residue was purified by column chromatography on silica gel, eluting with a stepwise gradient of 0-6% methanol in dichloromethane. Repurification of the pooled fractions on an acidic ion-exchange SPE cartridge afforded the free amine of the title compound 69NLS75 (1.10 g, 34%) as a colorless oil. The compound was dissolved in dichloromethane, treated with an excess of 2 M HCl in diethylether, precipitated from n-heptane, to afford the hydrochloride salt as a colorless solid in quantitative yield.

$R_f$=0.39 (MeOH/CH$_2$Cl$_2$ 1:9). LCMS m/z 441 [M+H]$^+$. $^1$H NMR (CDCl$_3$, free amine) δ 0.96 (d, 6H, J=6.8, CH$_3$), 1.24-1.32 (m, 1H, pip-H), 1.50 (m, 1H, pip-H), 1.62-1.70 (m, 1H, pip-H), 1.83 (m, 1H, pip-H), 1.96-2.06 (m, 1H, CH(CH$_3$)$_2$), 2.17 (s, 3H, NCH$_3$), 2.26-2.34 (m, 2H, pip-H), 2.46 (m, 1H, pip-H), 2.60 (m, 1H, pip-H), 2.70 (dd, 1H, J 7.3, 14.2, CH$_2$Ar$_F$), 2.85 (dd, 1H, J=6.6, 14.2, CH$_2$Ar$_F$), 3.34 (t, 1H, J=7.0, H-4), 3.57 (d, 1H, J=15.2, CH$_2$Ar$_{OiBu}$), 3.63 (d, 2H, J=6.6, OCH$_2$CH), 4.69 (d, 1H, J=15.2, CH$_2$Ar$_{OiBu}$), 6.73-6.97 (m, 8H, Ar—H). $^{13}$C NMR (CDCl$_3$) δ 19.5, 28.5, 31.3, 34.2, 36.8, 46.1, 46.3, 51.2, 51.3, 63.5, 74.7, 79.6, 114.9, 116.0 (d, J$_{C-F}$=21.0), 127.7, 129.6, 130.6 (d, J$_{C-F}$=7.7), 132.9 (d, J$_{C-F}$=3.4), 157.3, 159.2, 162.0 (d, J$_{C-F}$=244.0). HPLC t$_R$=10.4 min (method B).

3-(4-Cyclopropylmethoxybenzyl)-4-(4-fluorobenzyl)-8-methyl-1-oxa-3,8-diaza-spiro[4.5]decan-2-one, hydrochloride (69NLS52)

The title compound was obtained by a procedure similar to the one described for 69NLS75, from 69NLS44 and the appropriate benzylbromide derivative.

Alternatively, 69NLS44 can be first alkylated with 4-acetoxy benzylbromide, followed by basic treatment and alkylation of the resulting free hydroxyl function with cyclopropylmethyl bromide.

R$_f$=0.45 (MeOH/CH$_2$Cl$_2$ 1:9). LCMS m/z 439 [M+H]$^+$. $^1$H NMR (CD$_3$OD, free amine) δ 0.33 and 0.60 (2m, 4H, CH(CH$_2$)$_2$), 1.20-1.26 (m, 1H, CH(CH$_2$)$_2$), 1.37-1.45 (m, 1H, pip-H), 1.58 (m, 1H, pip-H), 1.79-1.86 (m, 1H, pip-H), 1.98 (m, 1H, pip-H), 2.26 (s, 3H, NCH$_3$), 2.34-2.42 (m, 2H, pip-H), 2.63 (m, 1H, pip-H), 2.77 (m, 1H, pip-H), 2.87 (dd, 1H, J=7.0, 14.2, CH$_2$Ar$_F$), 2.98 (dd, 1H, J=7.0, 14.2, CH$_2$Ar$_F$), 3.58 (t, 1H, J=7.0, H-4), 3.72 (d, 1H, J=15.2, CH$_2$Ar$_{OMecPr}$), 3.80 (d, 2H, J=6.8, OCH$_2$), 4.61 (d, 1H, J=15.2, CH$_2$Ar$_{OMecPr}$), 6.84-7.21 (m, 8H, Ar—H). HPLC t$_R$=6.5 min (method A).

4-(4-Fluorobenzyl)-3-(4-isobutoxybenzyl)-2-oxo-1-oxa-3,8-diaza-spiro[4.5]decane-8-carboxylic acid tert-butyl ester (69NLS77)

Preparation of 4-[1-Carboxy-2-(4-fluoro-phenyl)-ethyl]-4-hydroxy-piperidine-1-carboxylic acid tert-butyl ester (69NLS56)

n-Butyllithium (1.6 M in hexane, 8.8 mL, 14.0 mmol) was added dropwise under stirring over 5 min to a cooled solution of N,N-diisopropylamine (2.0 mL, 14.0 mmol) in THF (10 mL) at −40° C. The solution was warmed to 0° C. and a solution of 3-(4-fluoro-phenyl)propionic acid (1.18 g, 7.0 mmol) in THF (8 mL) was added. The mixture was stirred for 30 min at rt, cooled to −78° C. and N-BOC-4-piperidone (1.68 g, 8.4 mmol) in THF (7 mL) added dropwise over 15 min. The solution was allowed to warm to rt and poured into a stirred mixture of diethylether (100 mL) and water (50 mL). The organic layer was discarded, the aqueous layer extracted with another portion of diethylether. The aqueous layer was acidified with 2 M aq. HCl to pH 3.5 and extracted with dichloromethane (3×100 mL). The combined extracts were dried over Na$_2$SO$_4$, filtered and concentrated in vacuo, giving 69NLS56 as a yellow solid, which is used without further purification.

R$_f$=0.42 (MeOH/CH$_2$Cl$_2$ 1:19). LCMS m/z 268 [M-BOC+2H]$^+$. HPLC t$_R$=3.7 min (method B).

Preparation of 4-(4-fluorobenzyl)-2-oxo-1-oxa-3,8-diaza-spiro[4.5]decane-8-carboxylic acid tert-butyl ester (69NLS58).

The crude piperidine derivative 69NLS56 (ca. 7 mmol) was dissolved in toluene (100 mL), triethylamine (2.0 mL, 14.0 mmol) and diphenylphosphoryl azide (1.8 mL, 14.0 mmol) were added, and the mixture refluxed overnight. The solvent was removed in vacuo, the residue dissolved in ethyl acetate (200 mL) and washed with water and brine. The organic layer was dried over Na$_2$SO$_4$, filtered and evaporated to give 69NLS58. Purification of the residue on silica gel column chromatography, eluting with a stepwise gradient of 0-2% methanol in dichloromethane, afforded 69NLS58 as a yellow solid (1.47 g, 58% overall yield).

R$_f$=0.63 (MeOH/CH$_2$Cl$_2$ 1:19). R$_f$=0.33 (ethyl acetate/n-heptane 1:1). LCMS m/z 265 [M-BOC+2H]$^+$. HPLC t$_R$=10.3 min (method B).

Preparation of 4-(4-Fluorobenzyl)-3-(4-isobutoxybenzyl)-2-oxo-1-oxa-3,8-diaza-spiro[4.5]decane-8-carboxylic acid tert-butyl ester (69NLS77).

The title compound was obtained by alkylation of 4-(4-fluorobenzyl)-2-oxo-1-oxa-3,8-diaza-spiro[4.5]decane-8-carboxylic acid tert-butyl ester 69NLS58 (7.40 g, 20.3 mmol) with 4-isobutoxybenzylbromide (4.88 g, 20.3 mmol) following the same procedure as described for 69NLS75. After purification of the crude product on silica gel column chromatography, using a stepwise gradient of 0-60% ethyl acetate in n-heptane, the collected compound was dissolved in a minimum amount of ethyl acetate and precipitated from n-heptane, giving after filtration 69NLS77 (5.86 g, 55%) as a colorless solid.

R$_f$=0.64 (ethyl acetate/n-heptane 1:1). LCMS m/z 544 [M+NH$_4$]$^+$. $^1$H NMR (CDCl$_3$) δ 1.02 (d, 6H, J=6.6, CH$_3$), 1.36-1.60 (m, 12H, C(CH$_3$)$_3$, pip-H), 1.88 (m, 1H, pip-H), 2.05-2.11 (m, 1H, CH(CH$_3$)$_2$), 2.74 (dd, 1H, J=7.6, 14.2, CH$_2$Ar$_F$), 2.95 (dd, 1H, J=6.6, 14.2, CH$_2$Ar$_F$), 3.08 (m, 2H, pip-H), 3.39 (t, 1H, J=7.2, H-4), 3.66 (d, 1H, J=15.0, CH$_2$Ar$_{OiBu}$), 3.71 (d, 2H, J=6.6, OCH$_2$CH), 3.82 (m, 1H, pip-H), 3.92 (m, 1H, pip-H), 4.77 (d, 1H, J=15.0, CH$_2$Ar$_{OiBu}$), 6.82-7.03 (m, 8H, Ar—H). HPLC t$_R$=14.8 min (method B).

8-(2-[1,3]Dioxolan-2-yl-ethyl)-4-(4-fluorobenzyl)-3-(4-isobutoxybenzyl)-1-oxa-3,8-diaza-spiro[4.5]decan-2-one, hydrochloride (69NLS79-II)

69NLS77 (300 mg, 0.57 mmol) was N-BOC deprotected by treatment with a solution of TFA (2 mL) in dichlormethane (2 mL) at rt for 1.5 h. The solvent was removed in vacuo, the residue coevaporated twice with acetonitrile and redissolved in the same solvent (10 mL). Potassium carbonate (110 mg, 0.80 mmol) and 2-(2-bromoethyl)-1,3-dioxolane (80 µL, 0.68 mmol) were added, followed by sodium iodide (102 mg, 0.68 mmol) and the mixture stirred for 3 days at 50° C. Partitioning of the mixture between water and dichloromethane, extraction of the aqueous layer twice with dichloromethane, drying of the combined organic layers over Na$_2$SO$_4$, filtering and evaporation of the solvent gave crude 69NLS79-II. The residue was purified by silica gel column chromatography, eluting with a stepwise gradient of 0-4% methanol in dichloromethane, affording 69NLS79-II (127 mg, 0.24 mmol) as a colorless oil. The compound was converted to its HCl form by treatment with 2M HCl in diethylether as described above for 69NLS75, giving the salt as a colorless powder.

R$_f$=0.61 (MeOH/CH$_2$Cl$_2$ 1:9). LCMS m/z 527 [M+H]$^+$. $^1$H NMR (CD$_3$OD, free amine) δ 1.00 (d, 6H, J=6.6, CH$_3$), 1.34-1.42 (m, 1H, pip-H), 1.56 (m, 1H, pip-H), 1.72-1.81 (m, 3H, pip-H, O$_2$CHCH$_2$), 1.92 (m, 1H, pip-H), 1.97-2.06 (m, 1H, CH(CH$_3$)$_2$), 2.27-2.35 (m, 1H, pip-H), 2.44 (m, 2H, NCH$_2$), 2.63 (m, 1H, pip-H), 2.76 (m, 1H, pip-H), 2.85 (dd, 1H, J=7.0, 14.2, CH$_2$Ar$_F$), 2.95 (dd, 1H, J=7.0, 14.2, CH$_2$Ar$_F$), 3.60 (m, 1H, H-4), 3.69 (d, 2H, J=6.5, OCH$_2$CH), 3.70 (d, 1H, J=15.2, CH$_2$Ar$_{OiBu}$), 3.76-3.82 and 3.85-3.91 (2m, 4H, OCH$_2$), 4.60 (d, 1H, J=15.2, CH$_2$Ar$_{OiBu}$), 4.82 (t, 1H, J=4.7, O$_2$CH), 6.83-7.19 (m, 8H, Ar—H). HPLC t$_R$=11.3 min (method B).

4-(4-Fluorobenzyl)-3-(4-isobutoxybenzyl)-8-(3-morpholin-4-yl-propyl)-1-oxa-3,8-diaza-spiro[4.5]decan-2-one, dihydrochloride (69NLS83)

69NLS77 (300 mg, 0.57 mmol) was N-BOC deprotected as described in the preparation of 69NLS79-II and dissolved in acetonitrile (3 mL) and DMF (1 mL). To a solution of morpholine (65 μL, 0.74 mmol) in acetonitrile (3 mL) and DMF (1 mL) was added dropwise 1-chloro-3-iodopropane (73 μL, 0.68 mmol) and potassium carbonate (300 mg, 2.17 mmol). The mixture was heated at 50° C. for 3 h before the addition of the solution containing the deprotected spiropiperidine followed by sodium iodide (102 mg, 0.68 mmol). The mixture was stirred overnight at 50° C. and worked up as described for 69NLS79-II. Purification of the residue by silica gel column chromatography, eluting with a stepwise gradient of 0-6% methanol in dichloromethane, afforded the desired compound (127 mg, 40%) as a colorless oil. Treatment of the product in dichloromethane with 2 M HCl in diethylether as described for 69NLS75 gave the corresponding dihydrochloride salt as a colorless solid.

R$_f$=0.48 (MeOH/CH$_2$Cl$_2$ 1:9). LCMS m/z 554 [M+H]$^+$. $^1$H NMR (CD$_3$OD, free amine) δ 1.01 (d, 6H, J=6.9, CH$_3$), 1.36-1.43 (m, 1H, pip-H), 1.56-1.83 (m, 4H, pip-H, NCH$_2$CH$_2$), 1.94-2.06 (m, 2H, OCH$_2$CH, pip-H), 2.30-2.49 (m, 10H, pip-H, NCH$_2$CH$_2$O, NCH$_2$CH$_2$CH$_2$N), 2.68 (m, 1H, pip-H), 2.79-2.88 (m, 2H, pip-H, CH$_2$Ar$_F$), 2.97 (dd, 1H, J=6.8, 14.3, CH$_2$Ar$_F$), 3.56-3.74 (m, 8H, H-4, OCH$_2$CH, CH$_2$Ar$_{OiBu}$, NCH$_2$CH$_2$O), 4.60 (d, 1H, J=15.0, CH$_2$Ar$_{OiBu}$), 6.84-7.20 (m, 8H, Ar—H). HPLC t$_R$=10.2 min (method B).

4-(4-Fluorobenzyl)-3-(4-isobutoxybenzyl)-8-isopropyl-1-oxa-3,8-diaza-spiro[4.5]decan-2-one, hydrochloride (69NLS85)

69NLS77 (320 mg, 0.60 mmol) was N-BOC deprotected as described in the preparation of 69NLS79-II and dissolved in DMF (3 mL). Potassium carbonate (250 mg, 1.80 mmol) was added, followed by isopropylbromide (68 μL, 0.73 mmol)) and sodium iodide (110 mg, 0.73 mmol) and the mixture stirred overnight at 50° C. Workup was carried out as for 69NLS79-II. The residue was purified by silica gel column chromatography, eluting with a stepwise gradient of 0-6% methanol in dichloromethane, followed by repurification of the compound by acidic ion-exchange column, affording 69NLS85 (150 mg, 53%) as a colorless oil. The compound was converted to its hydrochloride form by treatment with 2M HCl in diethylether as described above, giving the salt as a colorless powder.

R$_f$=0.75 (MeOH/CH$_2$Cl$_2$ 1:9). LCMS m/z 469 [M+H]$^+$. $^1$H NMR (CD$_3$OD, free amine) δ 1.00 (d, 6H, J=6.7, CH$_3$), 1.01 (d, 6H, J=6.4, CH$_3$), 1.35-1.42 (m, 1H, pip-H), 1.56-1.60 (m, 1H, pip-H), 1.72-1.79 (m, 1H, pip-H), 1.93-2.06 (m, 2H, OCH$_2$CH, pip-H), 2.44-2.51 (m, 2H, pip-H), 2.59-2.75 (m, 3H, pip-H, NCH(CH$_3$)$_2$), 2.82-2.97 (m, 2H, CH$_2$Ar$_F$), 3.56 (t, 1H, J=6.8, H-4), 3.69-3.73 (m, 3H, OCH$_2$CH, CH$_2$Ar$_{OiBu}$), 4.61 (d, 1H, J=15.2, CH$_2$Ar$_{OiBu}$), 6.83-7.19 (m, 8H, Ar—H). HPLC t$_R$=1.0 min (method B).

4-(4-Fluorobenzyl)-3-(4-isobutoxybenzyl)-8-[2-(2-oxo-imidazolidin-1-yl)-ethyl]-1-oxa-3,8-diaza-spiro[4.5]decan-2-one, hydrochloride (38PH17-HCl)

The title compound was obtained as a colorless solid in 29% yield from 69NLS77 (180 mg, 0.34 mmol) following the same procedure as described for 69NLS85. Toluene-4-sulfonic acid 2-(2-oxo-imidazolidin-1-yl)-ethyl ester was used as the alkylating agent.

R$_f$=0.63 (MeOH/CH$_2$Cl$_2$ 1:9). LCMS m/z 539 [M+H]$^+$. $^1$H NMR (CD$_3$OD, free amine) δ 1.01 (d, 6H, J=6.8, CH$_3$), 1.34-1.42 (m, 1H, pip-H), 1.56 (m, 1H, pip-H), 1.77-1.85 (m, 1H, pip-H), 1.94 (m, 1H, pip-H), 1.99-2.07 (m, 1H, CH(CH$_3$)$_2$), 2.33-2.42 (m, 2H, pip-H), 2.55 (t, 2H, J=6.6, NCH$_2$CH$_2$), 2.71 (m, 1H, pip-H), 2.83-2.89 (m, 2H, pip-H, CH$_2$Ar$_F$), 2.97 (dd, 1H, J=7.0, 14.2, CH$_2$Ar$_F$), 3.25 (t, 2H, J=6.6, NCH$_2$CH$_2$), 2.89-3.36, 3.42-3.46 (2m, 4H, CONCH$_2$), 3.56 (t, 1H, J=7.0, H-4), 3.71 (d, 2H, J=6.4, OCH$_2$CH), 3.70 (d, 1H, J=15.0, CH$_2$Ar$_{OiBu}$), 4.60 (d, 1H, J=15.0, CH$_2$Ar$_{OiBu}$), 6.84-7.20 (m, 8H, Ar—H). HPLC t$_R$=10.0 min (method B).

4-(4-Fluorobenzyl)-3-(4-isobutoxybenzyl)-1-oxa-3,8-diaza-spiro[4.5]decan-2-one, hydrochloride (69NLS81)

69NLS77 (300 mg, 0.57 mmol) was N-BOC deprotected as described in the preparation of 69NLS79-II. The residue was purified by silica gel column chromatography, eluting with a stepwise gradient of 0-6% methanol in dichloromethane, and purification on an acidic ion-exchange SPE cartridge, afforded 69NLS81 (127 mg, 52%) as a colorless oil. Formation of the hydrochloride salt was carried out as before for 69NLS75 giving the title compound as a colorless solid.

R$_f$=0.29 (MeOH/CH$_2$Cl$_2$ 1:9). LCMS m/z 427 [M+H]$^+$. $^1$H NMR (CD$_3$OD, free amine) δ 1.00 (d, 6H, J=6.8, CH$_3$), 1.25-1.33 (m, 1H, pip-H), 1.52 (m, 1H, pip-H), 1.65-1.73 (m, 1H, pip-H), 1.91 (m, 1H, pip-H), 1.98-2.06 (m, 1H, CH(CH$_3$)$_2$), 2.73-2.97 (m, 6H, pip-H, CH$_2$Ar$_F$), 3.53 (t, 1H, J=7.0, H-4), 3.68-3.71 (m, 3H, OCH$_2$CH, CH$_2$Ar$_{OiBu}$), 4.59 (d, 1H, J=15.2, CH$_2$Ar$_{OiBu}$), 6.83-7.19 (m, 8H, Ar—H). HPLC t$_R$=9.7 min (method B).

8-Cyclopropylmethyl-4-(4-fluorobenzyl)-3-(4-isobutoxybenzyl)-1-oxa-3,8-diaza-spiro[4.5]decan-2-one, hydrochloride (38PH16-HCl)

The title compound was obtained as a colorless solid in 10% yield from 69NLS77 (180 mg, 0.34 mmol) following the same procedure as described for 69NLS85.

R$_f$=0.64 (MeOH/CH$_2$Cl$_2$ 1:9). LCMS m/z 481 [M+H]$^+$. $^1$H NMR (CD$_3$OD, free amine) δ 0.25, 0.62 (2m, 4H, CH(CH$_2$)$_2$), 0.92-0.99 (m, 1H, CH(CH$_2$)$_2$), 1.03 (d, 6H, J=6.6, CH$_3$), 1.52-1.59 (m, 1H, pip-H), 1.71 (m, 1H, pip-H), 1.89-2.15 (m, 3H, pip-H, CH(CH$_3$)$_2$), 2.60 (d, 2H, J=6.8, NCH$_2$), 2.73-2.80 (m, 2H, pip-H), 2.90 (dd, 1H, J=7.2, 14.4, CH$_2$Ar$_F$), 3.03 (dd, 1H, J=7.0, 14.4, CH$_2$Ar$_F$), 3.25-3.13 (m, 2H, pip-H), 3.66 (t, 1H, J=7.2, NCH), 3.73 (d, 1H, J=6.4, OCH$_2$CH), 3.76 (d, 1H, J=15.0, CH$_2$Ar$_{OiBu}$), 4.63 (d, 1H, J=15.0, CH$_2$Ar$_{OiBu}$), 6.85-7.23 (m, 8H, Ar—H). HPLC t$_R$=11.4 min (method B).

4-(4-Fluorobenzyl)-3-(4-isobutoxybenzyl)-8-ethyl-1-oxa-3,8-diaza-spiro[4.5]decan-2-one, hydrochloride (38-PH20)

9NLS77 (190 mg, 0.45 mmol) was N-BOC deprotected as described in the preparation of 69NLS79-II and dissolved in DMF (3 mL). Potassium carbonate (250 mg, 1.80 mmol) was added, followed by ethylbromide (50 µL, 0.45 mmol)) and the mixture stirred overnight at rt. Workup was carried out as for 69NLS79-II. The residue was purified by silica gel column chromatography, eluting with a stepwise gradient of 0-6% methanol in dichloromethane, followed by repurification of the compound by acidic ion-exchange SPE cartridge, to give 38-PH20 (77 mg, 38%) as a colourless oil. The compound was converted to its hydrochloride form by treatment with 2M HCl in diethylether as described above, giving the salt as a colorless powder.

$R_f$=0.52 (MeOH/CH$_2$Cl$_2$ 1:9). LCMS m/z 455 [M+H]$^+$. $^1$H NMR (CDCl$_3$, salt) δ 0.96 (d, 6H, J=6.6, CH$_3$), 1.39-1.55 (m, 6H, NCH$_2$CH$_3$, pip-H), 1.98-2.04 (m, 2H, pip-H, CH(CH$_3$)$_2$), 2.75-2.86 (m, 2H, CH$_2$Ar$_F$), 2.98 (m, 4H, NCH$_2$CH$_3$, pip-H), 3.19 (d, 1H, J=14.6, CH$_2$Ar$_{OiBu}$), 3.25-3.50 (m, 3H, pip-H, H-4), 3.62 (d, 2H, J=6.3, OCH$_2$CH), 4.60 (d, 1H, J=14.6, CH$_2$Ar$_{OiBu}$), 6.70-7.19 (m, 8H, Ar—H). HPLC $t_R$=4.7 min (method A).

3-(4-Difluoromethoxybenzyl)-4-(4-fluorobenzyl)-8-methyl-1-oxa-3,8-diaza-spiro[4.5]decan-2-one, hydrochloride (84AF8-30)

The title compound was obtained as a colourless solid in 25% yield from 69NLS44 (85 mg, 0.30 mmol) following the same procedure as described for 69NLS75.

$R_f$=0.44 (MeOH/CH$_2$Cl$_2$ 6:94). LCMS m/z 434 [M+H]$^+$. $^1$H NMR (CDCl$_3$, free amine) δ 1.42-1.50 (m, 1H, pip-H), 1.58-1.63 (m, 1H, pip-H), 1.76-1.83 (m, 1H, pip-H), 1.90-1.95 (m, 1H, pip-H), 2.28 (m, 3H, NCH$_3$), 2.37-2.45 (m, 2H, pip-H), 2.60 (m, 1H, pip-H), 2.72 (m, 1H, pip-H), 2.80 (dd, 1H, J=6.8, 14.4, CH$_2$Ar$_F$), 2.87 (dd, 1H, J=7.6, 14.4, CH$_2$Ar$_F$), 3.45 (t, 1H, J=6.8, NCH), 3.73 (d, 1H, J=15.2, CH$_2$Ar$_{OiBu}$), 4.71 (d, 1H, J=15.2, CH$_2$Ar$_{OiBu}$), 6.50 (t, 1H, J$_{C-F}$=73.6, CF$_2$H), 6.96-7.06 (m, 8H, Ar—H). HPLC $t_R$=2.7 min (method A).

8-Methyl-4-(4-methylbenzyl)-3-(4-trifluoromethoxybenzyl)-1-oxa-3,8-diaza-spiro[4.5]decan-2-one, hydrochloride (69NLS21)

Preparation of 4-[1-Carboxy-2-(4-methylphenyl)-ethyl]-4-hydroxy-1-methyl-piperidine (69NLS13)

The title compound was obtained in analogy with the procedure described for 69NLS42 starting with 3-(4-methylphenyl) propionic acid (0.70 g, 4.26 mmol).

$R_f$=0.14 (MeOH/CH$_2$Cl$_2$ 1:9).

Preparation of 4-(4-Methylbenzyl)-8-methyl-1-oxa-3,8-diaza-spiro[4.5]decan-2-one (69NLS15)

The title compound was obtained from 69NLS13 in analogy with the procedure described for 69NLS44.

$R_f$=0.5 (MeOH/CH$_2$Cl$_2$ 1:9). LCMS m/z 275 [M+H]$^+$. HPLC $t_R$=3.8 min (method B).

Preparation of 8-Methyl-4-(4-methylbenzyl)-3-(4-trifluoromethoxybenzyl)-1-oxa-3,8-diaza-spiro[4.5]decan-2-one, hydrochloride (69NLS21).

The title compound was obtained in 24% overall yield by alkylation of 69NLS15 with p-trifluoromethoxy benzylbromide, as described in the procedure for 69NLS75. Conversion of the free amine into the hydrochloride salt was performed as above, giving the title compound as a colourless solid.

$R_f$=0.26 (MeOH/CH$_2$Cl$_2$ 1:9). LCMS m/z 449 [M+H]$^+$. $^1$H NMR (CD$_3$OD, free amine) δ 1.46-1.53 (m, 1H, pip-H), 1.64 (m, 1H, pip-H), 1.81-1.89 (m, 1H, pip-H), 1.97 (m, 1H, pip-H), 2.24, 2.30 (2s, 6H, Ar—CH$_3$, NCH$_3$), 2.30-2.38 (m, 2H, pip-H), 2.63 (m, 1H, pip-H), 2.74 (m, 1H, pip-H), 2.85 (dd, 1H, J=6.7, 14.2, CH$_2$Ar$_{Me}$), 2.92 (dd, 1H, J=7.4, 14.2, CH$_2$Ar$_{Me}$), 3.67 (t, 1H, J=7.0, H-4), 3.90 (d, 11H, J=15.2, CH$_2$Ar$_{OCF3}$), 4.59 (d, 1H, J=15.2, CH$_2$Ar$_{OCF3}$), 7.03-7.21 (m, 8H, Ar—H). HPLC $t_R$=10.9 min (method B).

3-(4-Methoxybenzyl)-8-methyl-4-(4-methylbenzyl)-1-oxa-3,8-diaza-spiro[4.5]decan-2-one hydrochloride (69NLS35)

The title compound was obtained in 20% yield in analogy with the procedure described for 69NLS75 by alkylation of 69NLS15 with p-methoxy benzylchloride. In this case however, the reaction was performed at reflux for 3 h. Conversion of the free amine into the hydrochloride salt was performed as above, gave the title compound as a colorless solid.

$R_f$=0.45 (MeOH/CH$_2$Cl$_2$ 1:9). LCMS m/z 395 [M+H]$^+$. $^1$H NMR (CD$_3$OD, free amine) δ 1.33-1.41 (m, 1H, pip-H), 1.51-1.56 (m, 1H, pip-H), 1.77-1.85 (m, 1H, pip-H), 1.92-1.97 (m, 1H, pip-H), 2.22 and 2.30 (2s, 6H, Ar—CH$_3$, NCH$_3$), 2.27-2.36 (m, 2H, pip-H), 2.56 (m, 1H, pip-H), 2.70 (m, 1H, pip-H), 2.81 (dd, 1H, J=7.2, 14.2, CH$_2$Ar$_{Me}$), 2.94 (dd, 1H, J=7.0, 14.2, CH$_2$Ar$_{Me}$), 3.56 (t, 1H, J=7.0, H-4), 3.72 (d, 1H, J=15.2, CH$_2$Ar$_{OMe}$), 3.76 (s, 3H, OCH$_3$), 4.59 (d, 1H, J=15.2, CH$_2$Ar$_{OMe}$), 6.84-7.13 (m, 8H, Ar—H). HPLC $t_R$=6.2 min (method A).

(4R)- and (4S)-4-(4-fluorobenzyl)-3-(4-isobutoxybenzyl)-8-methyl-1-oxa-3,8-diaza-spiro[4.5]decan-2-one, hydrochloride (78NLS59 and 78NLS62)

The resolution of the racemate 69NLS44 was achieved by transient introduction of a camphanoyl chiral auxiliary. The resulting two diastereomers were separated by fractional crystallization, the camphanic acid substituent removed and the resulting spiropiperidines alkylated with the appropriate benzylbromide derivative.

Preparation of 3[(−)-Camphanoyl)]-4-(4-fluorobenzyl)-8-methyl-1-oxa-3,8-diaza-spiro[4.5]decan-2-one and separation of the two diastereomers (78NLS52-crys and 78NLS52-fil)

n-Butyllithium (2.7 M in heptane, 0.53 mL, 1.42 mmol) was added to a cooled solution of 69NLS44 (360 mg, 1.29 mmol) in THF (10 mL) at −78° C., and the mixture stirred for 30 min. A solution of (−)-camphanic acid chloride (307 mg, 1.42 mmol) in THF (2 mL) was added dropwise at −78° C., the solution stirred for 15 min at −78° C. and then 3 h at rt. Saturated ammonium chloride solution (5 mL) was added and the mixture extracted three times with ethyl acetate. The combined organic extracts were washed with sat. NaHCO$_3$ and brine, dried over Na$_2$SO$_4$, filtered and evaporated. The residue was crystallized from ethyl acetate/n-heptane at rt.

The light-yellow crystals 78NLS52-crys (155 mg, 26%, >98% de, determined by $^1$H NMR) were filtered off, the mother liquor concentrated and purified by silica gel column chromatography, eluting with a stepwise gradient of 0-2% methanol in dichloromethane. The second diastereomer is accumulated in the head fractions, which were evaporated and the residue recrystallized as before. Evaporation of the mother liquor afforded 78NLS52-fil (28 mg, 5%, 98% de determined by $^1$H NMR) as a colourless oil.

78NLS52-crys (>98% de): $R_f$=0.40 (MeOH/CH$_2$Cl$_2$ 1:9). LCMS m/z 459 [M+H]$^+$. $^1$H NMR (CDCl$_3$) δ 0.87, 1.09 and 1.15 (3s, 3×3H, CH$_3$), 1.45-1.53 (m, 1H, pip-H), 1.70-1.80 (m, 3H, pip-H, camph-H), 1.83-1.92 (m, 1H, camph-H), 1.97-2.02 (m, 1H, pip-H), 2.13-2.20 (m, 1H, camph-H), 2.24 (s, 3H, NCH$_3$), 2.29-2.38 (m, 2H, pip-H), 2.55-2.61 (m, 2H, pip-H, camph-H), 2.66 (m, 1H, pip-H), 2.80 (dd, 1H, J=9.0, 14.2, CH$_2$Ar), 3.06 (dd, 1H, J=4.9, 14.2, CH$_2$Ar), 4.59 (dd, 1H, J=4.9, 9.0, H-4), 6.98-7.25 (m, 4H, Ar—H). HPLC $t_R$=8.1 min (method B).

78NLS52-fil (98% de): $R_f$=0.40 (MeOH/CH$_2$Cl$_2$ 1:9). LCMS m/z 459 [M+H]$^+$. $^1$H NMR (CDCl$_3$) δ 0.98, 1.09 and 1.13 (3s, 3×3H, CH$_3$), 1.59-1.70 (m, 2H, pip-H), 1.73-1.80 (m, 1H, camph-H), 1.84-1.91 (m, 1H, camph-H), 1.97 (m, 2H, pip-H), 2.08-2.15 (m, 1H, camph-H), 2.25 (s, 3H, NCH$_3$), 2.24-2.37 (m, 2H, pip-H), 2.50-2.60 (m, 2H, pip-H), 2.94-3.01 (m, 2H, CH$_2$Ar, pip-H), 3.12 (dd, 1H, J=4.1, 14.2, CH$_2$Ar), 4.32 (dd, 1H, J=4.1, 9.0, H-4), 6.95-7.24 (m, 4H, Ar—H). HPLC $t_R$=8.7 min (method B).

Preparation of (4R)- and (4S)-4-(4-fluorobenzyl)-8-methyl-1-oxa-3,8-diaza-spiro[4.5]decan-2-one (78NLS57 and 78NLS61)

Lithium hydroxide monohydrate (20 mg, 0.47 mmol) was added to a solution of 78NLS52-crys (100 mg, 0.22 mmol) in THF/water (4 mL, 3:1) at 0° C. After stirring for 1 h at 0° C., sat. aq. NaHCO$_3$ was added (3 mL), the solution extracted three times with diethylether and the combined organic extracts dried over Na$_2$SO$_4$, filtered and evaporated. The crude compound 78NLS57 (60 mg) was used without further purification. In the same way, treatment of 78NLS52-fil (28 mg, 61 µmol) with lithiumhydroxide afforded 78NLS61.

Preparation of (4R)- and (4S)-4-(4-fluorobenzyl)-3-(4-isobutoxybenzyl)-8-methyl-1-oxa-3,8-diaza-spiro[4.5]decan-2-one, hydrochloride (78NLS59 and 78NLS62)

Alkylation of 78NLS57 (ca. 0.22 mmol) following the method described for 69NLS75 gave the enantiomer 78NLS59 (45 mg, 48%, over two steps). In the same way, alkylation of the second enantiomer 78NLS61 (ca. 61 µmol) gave 78NLS62 (7 mg, 25%, over two steps). Spectrochemical data for both compounds were identical with those determined for 69NLS75. The enantiomeric excess (ee) was determined to be 98% for 78NLS59 and 93% for 78NLS62 using chiral HPLC analysis (Chiracel OD-H column, 4.6×250 mm; hexane/I—PrOH/DEA 95:5:0.2; 0.5 mL/min; $t_R$ 20.8 and 23.6 min for 78NLS59 and 78NLS62 respectively).

Subsequent X-ray diffraction analysis of the intermediate 78NLS52-crys allowed the assignment of the (S)-configuration to the early eluting enantiomer (78NLS59, Formula II). Biological evaluation in vitro demonstrated that the (S)-enantiomer is the eutomer at the 5-HT2A receptor (Example 2, Table 1).

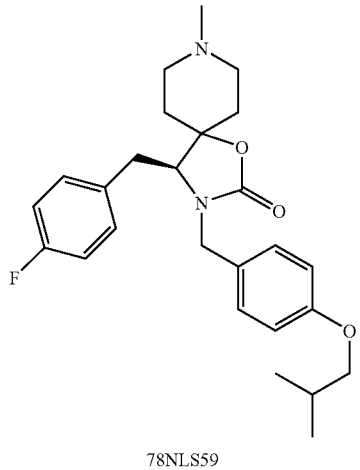

78NLS59

[2-(4-Fluorophenyl)ethyl]triphenylphosphonium bromide (78NLS66)

4-Fluorophenylethyl bromide (700 mg, 3.44 mmol) was dissolved in toluene (4 mL), triphenylphosphine (904 mg, 3.44 mmol) added and the solution heated for 10 min in a sealed flask at 200° C. under microwave heating. After cooling to rt, the solvent was decanted and the title compound was obtained quantitatively as the remaining glassy solid, which was used without further purification.

$R_f$=0.70 (MeOH/CH$_2$Cl$_2$ 1:9). $^1$H NMR (CDCl$_3$) δ 2.99-3.06 (m, 2H, PCH$_2$CH$_2$), 4.16-4.23 (m, 2H, PCH$_2$), 6.86-7.35 (m, 4H, Ar$_F$—H), 7.67-7.90 (m, 15H, PPh$_3$).

4-[2-(4-Fluorophenyl)ethylidene]-piperidine-1-carboxylic acid benzyl ester (103NLS05)

To a suspension of phosphonium bromide 78NLS66 (4.69 g, 10.1 mmol) in THF (100 mL) n-butyllithium (1.6 M in hexane, 6.3 mL, 10.1 mmol) was added at 0° C., giving a deep red solution. After stirring for 1 h at rt, a solution of benzyl 4-oxo-1-piperidinecarboxylate (2.24 g, 9.6 mmol) in THF (10 mL) was added dropwise over 30 min. The mixture was stirred at rt for 20 h, then water was added and the mixture extracted three times with diethylether. The combined organic layers were dried over Na$_2$SO$_4$, filtered and concentrated in vacuo. Purification of the residue by silica gel column chromatography, eluting with a stepwise gradient of 0-10% ethyl acetate in n-heptane, afforded the title compound (0.56 g, 17%) as a colourless oil.

$R_f$=0.63 (ethyl acetate/n-heptane 2:3). LCMS m/z 362 [M+Na]$^+$, 340 [M+H]$^+$. $^1$H NMR (CDCl$_3$) δ 2.24 (m, 2H, pip-H), 2.35 (m, 2H, pip-H), 3.37 (d, 2H, J=7.2, CH$_2$Ar$_F$), 3.55 (m, 4H, pip-H), 5.16 (s, 2H, OCH$_2$), 5.43 (t, 1H, J=7.2, CH=), 6.96-7.40 (m, 9H, Ar—H). HPLC $t_R$=10.7 min (method B).

2-(4-Fluorobenzyl)-1-oxa-6-aza-spiro[2.5]octane-6-carboxylic acid benzyl ester (103NLS09)

To a solution of the olefin 103NLS05 (79 mg, 0.23 mmol) in dichloromethane (3 mL) at 0° C. was added dropwise a solution of m-chloroperbenzoic acid (70% in H$_2$O, 69 mg, 0.28 mmol). The mixture was stirred at rt for 24 h, diluted with dichloromethane and washed with 10% aq. NaHCO$_3$ solution. The organic layer was dried over Na$_2$SO$_4$, filtered and evaporated to dryness. The title compound was obtained quantitatively and was used without further purification.

R$_f$=0.53 (ethyl acetate/n-heptane 2:3). LCMS m/z 356 [M+H]$^+$. $^1$H NMR (CDCl$_3$) δ 1.39 (m, 1H, pip-H), 1.66 (m, 1H, pip-H), 1.83-1.90 (m, 2H, pip-H), 2.79-2.92 (m, 2H, CH$_2$Ar$_F$), 3.03 (m, 1H, OCH), 3.39-3.45 (m, 2H, pip-H), 3.83-3.89 (m, 2H, pip-H), 5.16 (s, 2H, OCH$_2$), 6.98-7.36 (m, 9H, Ar—H). HPLC t$_R$=9.3 min (method B).

4-[1-Amino-2-(4-fluorophenyl)-ethyl]-4-hydroxypiperidine-1-carboxylic acid benzyl ester (103NLS28)

To a solution of ammonia in methanol (7 N, 5 mL) the crude epoxide 103NLS09 (520 mg, 1.40 mmol) was added and the solution heated for 20 h in a sealed flask at 100° C. After cooling to rt, the solvent was removed and the residue purified by C$_{18}$ reversed phase solid-phase extraction, eluting with a stepwise gradient of 0-80% methanol in dichloromethane, giving the aminoalcohol 103NLS28 (459 mg, 88%).

R$_f$=0.62 (MeOH/CH$_2$Cl$_2$ 1:9). LCMS m/z 373 [M+H]$^+$. $^1$H NMR (CDCl$_3$) δ 1.52-1.67 (m, 4H, pip-H), 2.37 (dd, 1H, J=11.3, 13.8, CH$_2$Ar$_F$), 2.70 (m, 3H, NH$_2$, OH), 2.81 (dd, 1H, J=2.9, 11.3, CH$_2$Ar$_F$), 2.97 (dd, 1H, J=2.9, 13.8, CHNH$_2$), 3.20-3.26 (m, 2H, pip-H), 4.03-4.08 (m, 2H, pip-H), 5.15 (s, 2H, OCH$_2$), 6.98-7.38 (m, 9H, Ar—H). HPLC t$_R$=5.5 min (method B).

5-(4-Fluorobenzyl)-3-oxo-1-oxa-4,9-diaza-spiro[5.5]undecane-9-carboxylic acid benzyl ester (103NLS30C)

The title compound was prepared from aminoalcohol 103NLS28 (303 mg, 0.81 mmol) according to literature procedures (Clark et al., *J. Med. Chem.* 26:855-861 (1983)), by acylation of the amino function with chloroacetylchloride, followed by halogen exchange with NaI and ring closure of the iodide derivative in presence of tert-butoxide. Purification of the crude product by silica gel column chromatography, eluting with a stepwise gradient of 0-100% ethyl acetate in n-heptane, afforded the title compound (64 mg, 19% overall yield) as a colourless solid.

R$_f$=0.19 (ethyl acetate/n-heptane 3:2). LCMS m/z 458 [M+H]$^+$. $^1$H NMR (CDCl$_3$) δ 1.52-1.74 (m, 2H, pip-H), 1.87-1.98 (m, 2H, pip-H), 2.47 (dd, 1H, J=11.7, 13.3, CH$_2$Ar$_F$), 2.81 (dd, 1H, J=2.7, 13.3, CH$_2$Ar$_F$), 3.04-3.22 (m, 2H, pip-H), 3.40-3.45 (m, 1H, H-5), 4.05-4.20 (m, 4H, H-2, pip-H), 5.15 (s, 2H, OCH$_2$Ph), 5.55 (s, 1H, NH), 6.99-7.37 (m, 9H, Ar—H). HPLC t$_R$=12.4 min (method B).

5-(4-Fluorobenzyl)-4-(4-isobutoxybenzyl)-3-oxo-1-oxa-4,9-diaza-spiro[5.5]undecane-9-carboxylic acid benzyl ester (103NLS33)

Alkylation of the spirocycle 103NLS30C (61 mg, 0.148 mmol) was performed as described in the preparation of 69NLS75 using 4-isobutoxybenzyl bromide 69NLS69 as the alkylating agent. After purification of the residue by silica gel column chromatography eluting with a stepwise gradient of 0-70% ethyl acetate in n-heptane, the title compound 103NLS33 (62 mg, 73%) was obtained as a colourless oil.

R$_f$=0.37 (ethyl acetate/n-heptane 1:1). LCMS m/z 575 [M+H]$^+$. $^1$H NMR (CDCl$_3$) δ 0.79-0.88 (m, 1H, pip-H), 1.02 (d, 6H, J=6.4, CH$_3$), 1.32-1.37 (m, 1H, pip-H), 1.69-1.81 (m, 2H, pip-H), 2.03-2.09 (m, 1H, CH(CH$_3$)$_2$), 2.72 (d, 1H, J=14.3, CH$_2$Ar$_{OiBu}$), 2.86-2.95 and 3.07-3.15 (2m, 5H, H-5, CH$_2$Ar$_F$, pip-H), 3.70 (d, 2H, J=6.4, OCH$_2$CH), 3.80-3.85 (m, 2H, pip-H), 4.16 (AB, 2H, J=17.6, H-2), 5.06 (s, 2H, OCH$_2$Ph), 5.35 (d, 1H, J=14.3, CH$_2$Ar$_{OiBu}$), 6.78-7.36 (m, 13H, Ar—H). HPLC t$_R$=10.9 min (method B).

5-(4-Fluorobenzyl)-4-(4-isobutoxybenzyl)-9-methyl-1-oxa-4,9-diaza-spiro[5.5]undecan-3-one (103NLS35)

The spirocycle 103NLS33 (62 mg, 0.107 mmol) in ethanol (5 mL) was N-CBz-deprotected by hydrogenation in presence of Pd/C (10%, 40 mg) under H$_2$-balloon pressure. The catalyst was filtered off and the filtrate evaporated under reduced pressure to give crude 5-(4-fluorobenzyl)-4-(4-isobutoxybenzyl)-1-oxa-4,9-diaza-spiro[5.5]undecan-3-one. The residue was dissolved in methanol (3 mL), formaldehyde (37% in water, 0.017 mL) added, followed by the addition of acetic acid (0.03 mL) and sodium cyanoborohydride (60 mg, 0.95 mmol). The solution was stirred at rt for 5 h, then water was added and the mixture basified with 2 N aq. NaOH solution. The mixture was extracted three times with dichloromethane, the combined organic layers washed with sat. ammonium chloride solution and brine, dried over Na$_2$SO$_4$, filtered and evaporated to dryness. The residue was purified by column chromatography on silica gel, eluting with a stepwise gradient of 0-7% methanol in dichloromethane, giving 103NLS35B (43 mg, 88% over both steps) as a colorless oil. The compound was converted to its HCl form by treatment with 2 M HCl in diethylether as described above for 69NLS75, affording the salt as a colorless powder.

R$_f$=0.50 (MeOH/CH$_2$Cl$_2$ 1:9). LCMS m/z 455 [M+H]$^+$. $^1$H NMR (CDCl$_3$) δ 0.94-1.06 (m, 7H, pip-H, CH$_3$), 1.50-1.57 (m, 1H, pip-H), 1.69-1.76 (m, 2H, pip-H), 2.00-2.09 (m, 2H, pip-H, CH(CH$_3$)$_2$), 2.22-2.29 (m, 4H, NCH$_3$, pip-H), 2.37-2.40 (m, 1H, pip-H), 2.55 (m, 1H, pip-H), 2.62 (d, 1H, J=14.3, CH$_2$Ar$_{OiBu}$), 2.87 (dd, 1H, J=7.8, 13.5, CH$_2$Ar$_F$), 3.06-3.14 (m, 2H, H-5, CH$_2$Ar$_F$, pip-H), 3.66 (d, 2H, J=6.4, OCH$_2$CH), 4.12 (AB, 2H, J=17.6, H-2), 5.29 (d, 1H, J=14.3, CH$_2$Ar$_{OiBu}$), 6.75-7.18 (m, 8H, Ar—H). HPLC t$_R$=7.5 min (method B).

3-Oxo-1,28-triaza-spiro[4.5]decane-8-carboxylic acid tert-butyl ester (84AF15)

A solution of hydrazine monohydrate (5.28 mL, 108.8 mmol) in n-butanol (20 mL) was added dropwise to a solution of N-BOC-4-methoxycarbonyl-methylenepiperidine (1.39 g, 5.44 mmol) in n-butanol (120 mL) at rt. The mixture was stirred for 15 h at 120° C. and the mixture allowed to cool to rt. The solvent was removed by evaporation under reduced pressure, the residue partitioned between ethyl acetate and water and the organic layer dried over sodium sulphate, filtered and evaporated to dryness. Purification of the residue by silica gel column chromatography, eluting with a stepwise gradient of 3-6% methanol in dichloromethane, afforded the desired compound (0.88 g, 63%) as white solid.

R$_f$=0.34 (MeOH/CH$_2$Cl$_2$ 6:94). LCMS m/z 200 [M+H-(t-Bu)]$^+$, 156 [M+H-BOC]$^+$. $^1$H NMR (CDCl$_3$) δ 1.45 (s, 9H, CH$_3$), 1.61-1.74 (m, 4H, pip-H), 2.34 (s, 2H, H-4), 3.38-3.52 (m, 4H, pip-H), 4.01 (s, 1H, NH), 7.15 (s, 1H, NH).

1-(4-Fluorobenzyl)-3-oxo-1,2,8-triaza-spiro[4.5]decane-8-carboxylic acid tert-butyl ester (84AF84-19)

4-Fluorobenzylbromide (0.37 mL, 2.97 mmol) was added dropwise to a solution of 84AF15 (289 mg, 1.13 mmol) in dry DMF (50 mL) at rt. The mixture was stirred at rt for 6 days under argon atmosphere. The solvent was removed by evaporation under reduced pressure and the residue partitioned between chloroform and water. The organic layer was dried over sodium sulphate, filtered and concentrated in vacuo. Purification of the residue by column chromatography on silica gel, eluting with dichloromethane, afforded the desired compound (160 mg, 39%).

$R_f$=0.53 (MeOH/$CH_2Cl_2$ 6:94). LCMS m/z 308 [M+H-BOC]$^+$, 364 [M+H]$^+$. $^1$H NMR ($CDCl_3$) δ 1.47 (s, 9H, $CH_3$), 1.71-1.76 (m, 2H, pip-H), 1.87-1.93 (m, 2H, pip-H), 2.45 (s, 2H, H-4), 3.31-3.38 (m, 2H, pip-H), 3.64-3.70 (m, 2H, pip-H), 3.80 (s, 2H, $CH_2Ar_F$), 6.62 (s, 1H, NH), 7.01-7.30 (m, 4H, Ar—H).

1-(4-Fluorobenzyl)-2-(4-isobutoxybenzyl)-3-oxo-1,2,8-triaza-spiro[4.5]decane-8-carboxylic acid tert-butyl ester (118AF94-23)

NaH (24 mg, 0.50 mmol) was added slowly to a solution of 84AF84-19 (0.149 g, 0.41 mmol) in dry DMF (5 mL) and the mixture stirred at rt for 30 min. A solution of 4-isobutoxybenzyl bromide 69NLS69 (117 mg, 0.48 mmol) in dry DMF (1 mL) was added dropwise to the mixture. After 1 h stirring at rt the mixture was partitioned between ethyl acetate and water. The organic layer was dried over sodium sulphate, filtered and concentrated in vacuo. Purification of the residue by column chromatography on silica gel, eluting with a stepwise gradient of 3-6% methanol in dichloromethane, followed by preparative reversed phase HPLC ($C_{18}$) afforded the desired compound (109 mg, 50%).

$R_f$=0.51 (MeOH/$CH_2Cl_2$ 1:99). LCMS m/z 526 [M+H]$^+$, 470 [M+H-(t-Bu)]$^+$. $^1$H NMR ($CDCl_3$) δ 1.00 (d, 6H, J=6.8, $CH(CH_3)_2$), 1.35 (m, 4H, pip-H), 1.40 (s, 9H, $O(CH_3)_3$), 2.06 (m, 1H, $CH(CH_3)_2$), 2.41 (s, 2H, H-4), 3.08-3.15 (m, 2H, pip-H), 3.22-3.29 (m, 2H, pip-H), 3.67 (d, 2H, J=6.4, $OCH_2$), 3.92 (m, 4H, $CH_2Ar_F$, $CH_2Ar_{OiBu}$), 6.77-7.37 (m, 8H, Ar—H).

1-(4-Fluorobenzyl)-2-(4-isobutoxybenzyl)-1,2,8-triaza-spiro[4.5]decane-3-one (84AF99-24)

118AF94-23 (100 mg, 0.21 mmol) was N-BOC deprotected as described in the preparation of 69NLS79-II to give the title compound, which was used without further purification.

$R_f$=0.40 (MeOH/$CH_2Cl_2$ 1:9). LCMS m/z 426 [M+H]$^+$. $^1$H NMR ($CDCl_3$) δ 0.99 (d, 6H, J=6.4, $CH(CH_3)_2$), 1.35 (m, 4H, pip-H), 1.49 (s, 1H, NH), 2.00-2.05 (m, 1H, $CH(CH_3)_2$), 2.42 (s, 2H, H-4), 2.50 (m, 2H, pip-H), 2.76 (m, 2H, pip-H), 3.66 (d, 2H, J=6.4, $OCH_2$), 3.92 (s, 2H, $CH_2Ar$), 3.95 (s, 2H, $CH_2Ar$), 6.75-7.34 (m, 8H, Ar—H).

1-(4-Fluorobenzyl)-2-(4-isobutoxybenzyl)-8-methyl-1,2,8-triaza-spiro[4.5]decane-3-one, Hydrochloride (84AF100-25)

The desired spirocycle was obtained from 84AF99-24 (60 mg, 0.14 mmol) following the same procedure described for the preparation of 103NLS35. Formation of the hydrochloride salt was carried out as for 69NLS75 giving the title compound (39 mg, 63%) as a colourless solid.

$R_f$=0.57 (MeOH/$CH_2Cl_2$ 1:9). LCMS m/z 440 [M+H]$^+$. $^1$H NMR ($CDCl_3$) δ 0.94 (d, 6H, J=6.4, $CH(CH_3)_2$), 1.38-1.68 (m, 4H, pip-H), 1.96-2.02 (m, 1H, $CH(CH_3)_2$), 2.23-2.46 (m, 9H, pip-H, $NCH_3$, H-4), 3.61 (d, 2H, J=6.4, $OCH_2$), 3.85 (m, 4H, $CH_2Ar_{OiBu}$, $CH_2Ar_F$), 6.70-7.28 (m, 8H, Ar—H).

8-(2-[1.3]-Dioxan-2-yl-ethyl)-4-(4-fluorobenzyl)-3-(4-isobutoxy-benzyl)-1-oxa-3,8-diaza-spiro[4.5]decane-2-one, Oxalate (118AF02-74)

69NLS77 was N-BOC deprotected as described in the preparation of 69NLS79-II and the resulting compound (172 mg, 0.40 mmol) alkylated with 2-(2-bromoethyl)-1,3-dioxane following the same procedure as for the preparation of 69NLS85. Conversion of the compound (139 mg, 64%) into its oxalate salt form gave the title compound as a colourless solid.

$R_f$=0.33 (MeOH/$CH_2Cl_2$ 1:24). LCMS m/z 541 [M+H]$^+$. $^1$H NMR ($CDCl_3$) δ 1.00 (d, 6H, J=6.8, $CH(CH_3)_2$), 1.23-1.36 (m, 2H, pip-H, dioxane-H), 1.54-1.66 (m, 1H, pip-H), 1.67-1.74 (m, 3H, $CH_2CH_2N$, pip-H), 1.86-1.90 (m, 1H, pip-H), 1.97-2.15 (m, 2H, dioxane-H, $CH(CH_3)_2$), 2.31-2.43 (m, 4H, $CH_2CH_2N$, pip-H), 2.55 (m, 1H, pip-H), 2.69 (m, 1H, pip-H), 2.71-2.89 (m, 2H, $CH_2Ar_F$), 3.36 (t, 1H, J=6.8, H-4), 3.56 (d, 1H, J=15.2, $CH_2Ar_{OiBu}$), 3.67-3.74 (m, 4H, $OCH_2CH(CH_3)_2$, dioxane-H), 4.03-4.07 (m, 2H, dioxane-H), 4.51 (t, 1H, J=5.2, OCHO), 4.72 (d, 1H, J=15.2, $CH_2Ar_{OiBu}$), 6.79-7.04 (m, 8H, Ar—H).

4-(4-Fluorobenzyl)-3-(4-isobutoxy-benzyl)-8-{3-[(S)-4-isopropyl-2-oxo-oxazolidin-3-yl]-propyl}-1-oxa-3,8-diaza-spiro[4.5]decane-2-one, oxalate (118AF04-75)

69NLS77 was N-BOC deprotected as described in the preparation of 69NLS79-II and the resulting compound (172 mg, 0.40 mmol) alkylated with (4S)-3-(3-chloropropyl)-4-isopropyl-2-oxazolidin-2-one in DMF (3 mL) in presence of sodium iodide (72 mg, 0.48 mmol), following the same procedure as for the preparation of 69NLS85. Conversion of the compound (130 mg, 55%) into its oxalate salt form gave the title compound as a colourless solid.

$R_f$=0.29 (MeOH/$CH_2Cl_2$ 1:19). LCMS m/z 596 [M+H]$^+$. $^1$H NMR ($CDCl_3$) δ 0.84-0.88 (m, 6H, $CH_{3iPr}$, 1.01 (d, 6H, J=6.8, $CH_{3iBu}$), 1.24-1.34 (m, 1H, pip-H), 1.55-1.74 (m, 4H, pip-H, $CH_{2chain}$), 1.87-1.93 (m, 1H, pip-H), 1.97-2.13 (m, 2H, $CH_{OiBu}$, $CH_{iPr}$), 2.27-2.40 (m, 4H, pip-H, $NCH_{2chain}$), 2.56 (m, 1H, pip-H), 2.69 (m, 1H, pip-H), 2.75-2.80 (m, 1H, $CH_2Ar_F$), 2.87-2.98 (m, 2H, $CH_2Ar_F$, $NCH_{2chain}$), 3.37 (t, 1H, J=6.8, H-4), 3.48-3.55 (m, 1H, $NCH_{2chain}$), 3.58-3.64 (m, 1H, $CH_2Ar_{OiBu}$), 3.65-3.71 (m, 3H, $OCH_2CH(CH_3)_2$, $CH_{isox}$), 4.00-4.04 (m, 1H, $OCH_{isox}$), 4.11-4.16 (m, 1H, $OCH_{isox}$), 4.75 (d, 1H, J=15.2, $CH_2Ar_{OiBu}$), 6.80-7.03 (m, 8H, Ar—H).

Example 2

Pharmacological Data

Receptor Selection and Amplification (R-SAT) Assays.

The functional receptor assay, Receptor Selection and Amplification Technology (R-SAT), was used (with minor modifications from that previously described U.S. Pat. No. 5,707,798) to screen compounds for efficacy at the 5-HT2A receptor. Briefly, NIH3T3 cells were grown in 96 well tissue culture plates to 70-80% confluence. Cells were transfected for 12-16 hours with plasmid DNAs using superfect (Qiagen Inc.) as per manufacture's protocols. R-SAT's were generally performed with 50 ng/well of receptor and 20 ng/well of Beta-galactosidase plasmid DNA-All receptor and G-protein constructs used were in the pSI mammalian expression vector (Promega Inc) as described in U.S. Pat. No. 5,707,798. The 5HT2A receptor gene was amplified by nested PCR from brain cDNA using the oligodeoxynucleotides based on the published sequence (see Saltzman et. al. *Biochem. Biophys. Res. Comm.* 181:1469-78 (1991)). Large-scale transfections, cells were transfected for 12-16 hours, then trypsinized and frozen in DMSO. Frozen cells were later thawed, plated at 10,000-40,000 cells per well of a 96 well plate that contained drug. With both methods, cells were then grown in a humidified atmosphere with 5% ambient CO2 for five days. Media was then removed from the plates and marker gene activity was measured by the addition of the beta-galactosidase substrate ONPG (in PBS with 5% NP-40). The resulting calorimetric reaction was measured in a spectrophotometric plate reader (Titertek Inc.) at 420 nM. All data were analyzed using the computer program XLFit (IDBSm). Efficacy is the percent maximal repression compared to repression by a control compound (ritanserin in the case of 5HT2A). pIC50 is the negative of the log(IC50), where IC50 is the calculated concentration in Molar that produces 50% maximal repression. The results obtained for several compounds of the invention are presented in Table 1, below.

TABLE 1

Efficiency and pIC50 of Compounds at the 5-HT2A Receptor Compared to Ritanserin

| Compound ID | 5HT2A pIC$_{50}$ | N IC$_{50}$ | STD DEV | 5HT2A % inhibition | N % inhibition | Std Dev % inhibition |
|---|---|---|---|---|---|---|
| 69NLS21 | 9.1 | 4 | 0.5 | 83 | 4 | 11 |
| 69NLS35 | 9.6 | 7 | 0.2 | 103 | 7 | 20 |
| 69NLS75 | 9.5 | 15 | 0.3 | 94 | 16 | 22 |
| 69NLS52 | 9.6 | 7 | 0.3 | 87 | 7 | 14 |
| 69NLS79-II | 8.1 | 4 | 0.2 | 101 | 4 | 12 |
| 69NLS81 | 8.3 | 4 | 0.1 | 85 | 4 | 10 |
| 69NLS83 | 8 | 4 | 0.1 | 85 | 4 | 10 |
| 69NLS85 | 9.1 | 4 | 0.3 | 95 | 8 | 9 |
| 38-PH16-HCl | 8.1 | 4 | 0.2 | 95 | 4 | 18 |
| 38-PH17-HCl | 8.8 | 5 | 0.3 | 84 | 8 | 12 |
| 38-PH20 | 9.3 | 5 | 0.3 | 100 | 10 | 9 |
| 78NLS59 | 9.6 | 17 | 0.3 | 98 | 22 | 19 |
| 78NLS62 | 8.2 | 5 | 0.3 | 89 | 4 | 7 |

Selectivity Profile for 4-(4-Fluorobenzyl)-3-(4-isobutoxybenzyl)-8-methyl-1-oxa-3,8-diaza-spiro[4.5]decan-2-one (69NLS75)

The R-SAT assay (described above in example) was used to investigate the selectivity of 4-(4-Fluoro-benzyl)-3-(4-isobutoxy-benzyl)-8-methyl-1-oxa-3,8-diaza-spiro[4.5]decan-2-one. The results from a broad profiling of this compound at a variety of receptors are reported in Table 2 below. NR means No Response, i.e. the compound investigated showed no effect at the receptor studied.

TABLE 2

Selectivity of 4-(4-Fluorobenzyl)-3-(4-isobutoxybenzyl)-8-methyl-1-oxa-3,8-diaza-spiro[4.5]decan-2-one 69NLS75

| Receptor | Assay | pEC50 or pIC50 |
|---|---|---|
| 5HT2A | agonist | NR |
|  | inverse | 9.5 (94%) |
| 5HT2B | agonist | NR |
|  | inverse | <5.6 |
|  | antagonist | NR |
| 5HT 2C | agonist | NR |
|  | inverse | 7.5 (77%) |
| 5HT1A | agonist | NR |
|  | antagonist | 6.4 |
| 5HT1B | agonist | NR |
|  | antagonist | <5.5 |
| 5HT1D | agonist | NR |
|  | antagonist | <6.25 |
| 5HT1E | agonist | NR |
|  | antagonist | <6.2 |
| 5HT1F | agonist | NR |
|  | antagonist | NR |
| 5HT6A | inverse | NR |
| 5HT7A | agonist | NR |
|  | inverse | NR |
| D1 | agonist | NR |
|  | antagonist | NR |
| D2 | agonist | NR |
|  | antagonist | NR |
| D3 | agonist | NR |
|  | antagonist | NR |
| m1 | agonist | NR |
| m2 | agonist | NR |
| m3 | agonist | NR |
|  | inverse | NR |
|  | antagonist | 6.4 |
| m4 | agonist | <5.5 |
| m5 | agonist | NR |
| H1 | agonist | NR |
|  | antagonist | 6.7 |
| alpha 2A | agonist | NR |
|  | antagonist | 6.3 |
| alpha 2B | agonist | NR |
|  | antagonist | NR |
| alpha 2C | agonist | NR |
|  | antagonist | <5.5 |
| alpha 1B | agonist | NR |
|  | antagonist | NR |

TABLE 2-continued

Selectivity of 4-(4-Fluorobenzyl)-3-(4-isobutoxybenzyl)-8-methyl-1-oxa-3,8-diaza-spiro[4.5]decan-2-one 69NLS75

| Receptor | Assay | pEC50 or pIC50 |
| --- | --- | --- |
| oprk 1 | agonist | NR |
|  | antagonist | NR |

Example 3

In Vivo Pharmacology of 4-(4-Fluorobenzyl)-3-(4-isobutoxybenzyl)-8-methyl-1-oxa-3,8-diaza-spiro[4.5]decan-2-one (69NLS75)

Methods

Animals and Apparatus

Male Non-Swiss Albino mice (Harlan Sprague-Dawley) were housed (4 mice/cage) in rooms with temperature and humidity controlled and water and food (Harlan Teklad) freely available. Mice were kept on a 12-hr light:dark cycle. For locomotor experiments, plastic 20×20×30 cm activity cages were equipped with photocell beams (AccuScan Instruments).

Procedure

Locomotor Activity

For hyperactivity experiments, mice were treated with 0.3 mg/kg dizocilpine i.p. 15 min before the session. Mice were treated with 69NLS75 s.c. 10 min before the session or p.o. 30 min before the session and placed into the activity cages. For spontaneous activity, 69NLS75 was administered alone. Locomotor data were collected during a 15 min session without habituation in a lit room. Each dose combination was tested in a separate group of animals (n=8). Distance traveled (cm) was calculated and averaged followed by ANOVA and post-hoc Dunnett's t-test comparisons.

Results

69NLS75 caused a dose-related decrease in MK-801-induced hyperactivity in mice consistent with antipsychotic efficacy. A statistically significant decrease compared to vehicle control occurred at 3 mg/kg after both s.c. and p.o. administration suggesting excellent oral bioavailability. In addition, the attenuation of MK-801 hyperactivity occurred at doses that had no effect on spontaneous locomotor activity, indicating no motor side effects at efficacious doses.

Example 4

In Vivo Pharmacology of Additional Compounds

The effect of various compounds on locomotor activity in mice treated with MK801 was observed as described above.

Animals received 0.1-30 mg/kg of the compound indicated via subcutaneous injection or oral administration. MED indicates the minimum effective dose at which a statistically significant reduction of locomotor activity (described above) was observed. MED=minimum effective dose in vivo.

TABLE 4

Comparison Of Analogs For Their Ability To Attenuate MK801-Induced Hyperactivity In Mice.

| Compound | MED (mg/kg) s.c. | MED (mg/kg) p.o. |
| --- | --- | --- |
| 69NLS52 | n.d. | 10 |
| 69NLS75 | 3 | 3 |
| 69NLS79-II | n.d. | 3 |

What is claimed is:

1. A compound of formula I, salts and stereoisomers thereof:

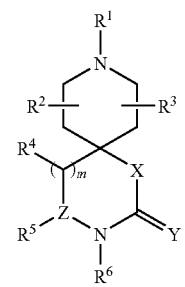

I wherein X is N(R$^N$); wherein R$^N$ is selected from hydrogen and C$_{1-6}$ alkyl;

Y is selected from the group consisting of O and S;

Z is CH;

R$^1$ is hydrogen, or an optionally substituted substituent selected from the group consisting of C$_{1-6}$ alkyl, C$_{2-8}$ alkenyl, C$_{2-8}$ alkynyl, C$_{3-8}$ cycloalkyl, aryl, heteroaryl, aryl(C$_{1-6}$ alkyl), heteroaryl(C$_{1-6}$ alkyl), heterocyclyl(C$_{1-6}$ alkyl), hydroxy(C$_{1-6}$ alkyl), amino(C$_{1-6}$ alkyl), and halo(C$_{1-6}$ alkyl);

m is 0 and R$^4$ is absent;

R$^5$ and R$^6$ are independently an optionally substituted substituent selected from the group consisting of aryl(C$_{1-6}$ alkyl), heteroaryl(C$_{1-6}$ alkyl), and heterocyclyl(C$_{1-6}$ alkyl), R$^2$ and R$^3$ are independently selected from the group consisting of hydrogen, halogen, hydroxy, and optionally substituted C$_{1-6}$ alkyl or selected such that R$^2$ and R$^3$ together form a ring system such that

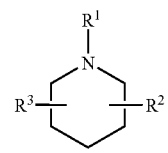

is selected from the group consisting of

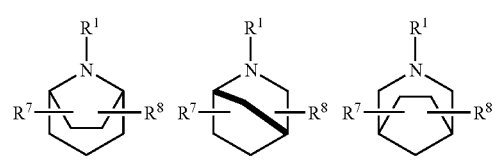

-continued

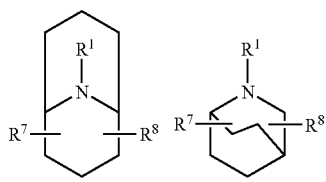

wherein $R^7$ and $R^8$ are independently selected from the group consisting of hydrogen, halogen, hydroxy, and $C_{1-6}$ alkyl.

2. The compound of claim 1, wherein $R^1$ is selected from the group consisting of $C_{1-6}$ alkyl, $C_{2-8}$ alkenyl, $C_{2-8}$ alkynyl, and $C_{3-8}$ cycloalkyl.

3. The compound of claim 2, wherein Y is O.

4. The compound of claim 3, wherein $R^2$ and $R^3$ are both hydrogen.

5. The compound of claim 4, wherein $R^5$ and $R^6$ are independently selected from the group consisting of an optionally substituted aryl($C_{1-6}$ alkyl) and an optionally substituted heteroaryl($C_{1-6}$ alkyl).

6. The compound of claim 5, wherein $R^5$ and $R^6$ are each an optionally substituted aryl($C_{1-6}$ alkyl).

7. The compound of claim 6, wherein $R^5$ and $R^6$ are each an optionally substituted benzyl.

8. A composition comprising:
    i) one or more compounds of formula I, according to claim 1; and
    ii) at least one pharmaceutically acceptable excipient or carrier.

9. A method of treating a disease condition associated with a serotonin receptor comprising administering to a subject in need of such treatment a therapeutically effective amount of one or more of the compounds of claim 1, wherein the disease condition is selected from the group consisting of: schizophrenia, psychosis, drug-induced psychosis, treatment-induced psychosis, migraine, hypertension, thrombosis, vasospasm, depression, anxiety, a sleep disorder and an appetite disorder.

10. The compound of claim 6, wherein $R^5$, and $R^6$ are each a mono-substituted aryl($C_{1-6}$ alkyl) group.

11. The compound of claim 10, wherein $R^1$ is selected from the group consisting of $C_{1-6}$ alkyl, $C_{2-8}$ alkenyl, $C_{2-8}$ alkynyl and $C_{3-8}$ cycloalkyl.

12. The compound according of claim 10, wherein said aryl($C_{1-6}$ alkyl) is (4-substituted)-aryl($C_{1-6}$ alkyl).

13. The compound of claim 10, wherein $R^5$, and $R^6$ are different mono-substituted aryl($C_{1-6}$ alkyl) groups.

14. The compound of claim 1, wherein $R^1$ is selected from the group consisting of aryl($C_{1-6}$ alkyl), heteroaryl($C_{1-6}$ alkyl) and heterocyclyl($C_{1-6}$ alkyl).

15. The compound of claim 1, wherein $R^1$ is selected from the group consisting of hydroxy($C_{1-6}$ alkyl), amino($C_{1-6}$ alkyl), and halo($C_{1-6}$ alkyl).

16. The compound of claim 1, wherein $R^1$ is selected from the group consisting of aryl and heteroaryl.

* * * * *